(12) United States Patent
Seong et al.

(10) Patent No.: US 7,592,457 B2
(45) Date of Patent: Sep. 22, 2009

(54) 3-ARYL-3-METHYL-QUINOLINE-2, 4-DIONES, PREPARATION METHOD THEREOF, AND PHARMACEUTICAL COMPOSITION CONTAINING THE SAME

(75) Inventors: Churlmin Seong, Daejeon (KR); Nosang Park, Daejeon (KR); Yungsik Jung, Daejeon (KR); Jinil Choi, Daejeon (KR); Wookyu Park, Chungcheongbuk-do (KR); Heeyung Cho, Daejeon (KR); Jaeyang Kong, Daejeon (KR); Daeyoung Jung, Daejeon (KR); Sunhee Kang, Daejeon (KR); Sukjin Song, Busan (KR); Kyungran Kwark, Busan (KR)

(73) Assignee: Korea Research Institute of Chemical Technology, Daejeon (KR)

( * ) Notice: Subject to any disclaimer, the term of this patent is extended or adjusted under 35 U.S.C. 154(b) by 444 days.

(21) Appl. No.: 11/242,665

(22) Filed: Oct. 4, 2005

(65) Prior Publication Data
US 2006/0084676 A1    Apr. 20, 2006

(30) Foreign Application Priority Data
Oct. 20, 2004    (KR) .................... 10-2004-0084081

(51) Int. Cl.
*C07D 215/38*    (2006.01)
(52) U.S. Cl. .................................. 546/155
(58) Field of Classification Search .................. 546/155
See application file for complete search history.

(56) References Cited

U.S. PATENT DOCUMENTS 3,133,928 A * 5/1964 Wiggins et al. ............. 546/155

OTHER PUBLICATIONS

Nishimura et al. STN Accession No.1970:477020; Document No. 3:77020, Abstract of Yakugaku Zasshi (1970), 90(7), 818-28.*
Hoyer, D. et al., Pharmacol. Biochem. Behav. 71:533-554, 2002.
Kroeze, W. K. et al., Curr. Top. Med. Chem. 2:507-528, 2002.
Kohen, R. et al., J. Neurochem. 66:47-56, 1996.
Roth, B. L. et al., J. Pharmacol. Exp. Ther. 268:1403-1410, 1994.
Sleight, A. J. et al., Br. J. Pharmacol. 124:556-562, 1998.
Bromidge, S. M. et al., J. Med. Chem. 42:202-205, 1999.
Glennon, R. A. et al., J. Med. Chem. 43:1011-1018, 2000.
Vogt, I. R. et al., Am. J. Med. Genet. 96:217-221, 2000.
Bourson, A. et al., J. Pharmacol. Exp. Ther. 274:173-180, 1995.
Sleight, A. J. et al., Neuropharmacology 41:210-219, 2001.
Rogers, D. C. et al., Psychopharmacology (Berlin) 158:114-119, 2001.
Russell, M. G. N. And Dias, R., Curr. Top. Med. Chem. 2:643-654, 2002.
Stean, T. O. et al., Pharmacol. Biochem. Behav. 71:645-654, 2002.

* cited by examiner

*Primary Examiner*—D. Margaret Seaman
*Assistant Examiner*—Nizal S Chandrakumar
(74) *Attorney, Agent, or Firm*—Lucas & Mercanti, LLP

(57) ABSTRACT

The present invention relates to compounds of 3-aryl-3-methyl-quinoline-2,4-diones acting as a 5HT6 receptor antagonist, a preparation method thereof, and a pharmaceutical composition containing the same for treatment of the central nervous system disorders. The compounds of 3-aryl-3-methyl-quinoline-2,4-diones according to the present invention may be valuably used for treatment of a 5HT6 receptor relating disorders because of its excellent binding affinity for the 5HT6 receptor and excellent selectivity for the 5HT6 receptor over other receptors.

4 Claims, 5 Drawing Sheets

Sal: Saline
Meth: Methamphetamine (2mg/kg)

Sal: Saline
Meth: Methamphetamine (2mg/kg)

Sal: Saline
Meth: Methamphetamine(2mg/kg)

Sal: Saline
Meth: Methamphetamine(2mg/kg)

3-ARYL-3-METHYL-QUINOLINE-2, 4-DIONES, PREPARATION METHOD THEREOF, AND PHARMACEUTICAL COMPOSITION CONTAINING THE SAME

This patent application claims the benefit of priority from Korean Patent Application No. 10-2004-0084081 filed Oct. 20, 2004, the contents of which are incorporated herein by reference.

BACKGROUND OF THE INVENTION

1. Field of the Invention

The present invention relates to 3-aryl-3-methyl-quinoline-2,4-diones acting as a 5-HT6 receptor antagonist, a preparation method thereof, and a pharmaceutical composition containing the same for treatment of central nervous system disorders.

2. Description of the Prior Art

Although the function of serotonin (5-HT) in the central nervous system is still being clarified, various studies have indicated 5-HT has been implicated in the aetiology of many disease states and may be particularly important in mental illness, such as depression, anxiety, schizophrenia, eating disorders, obsessive compulsive disorder (OCD), migraine and panic disorder. Recent advances in pharmacology, molecular biology, and genetics on the serotonin system hold out the promise of the development of improved pharmacological treatment for some aspects of neurological diseases. Indeed, many currently used treatments of these disorders are thought to act by modulating serotonergic neurons. During the last decade, multiple 5-HT receptor subtypes have been characterized. Initially, receptor subtypes were characterized using pharmacological tools only. On the basis of the receptor binding profiles, common secondary messenger coupling and the functional activity of ligands, four main subgroups of 5-HT receptors, termed 5-HT1, 5-HT2, 5-HT3 and 5-HT4, were identified. More recently, molecular biological techniques have both confirmed this classification, in that each subgroup has been found to have relatively dissimilar protein structures, and led to the identification of novel 5-HT receptors (5-HT1F, 5-HT5, 5-HT6 and 5-HT7) enabling them to be cloned, expressed in cultured cell lines [Hoyer, D. et al., *Pharmacol. Biochem. Behav.* 2002, 71, 533-554; Kroeze, W. K. et al., *Curr. Top. Med. Chem.* 2002, 2, 507-528].

Most recently, the 5-HT6 receptor has been cloned from rat cDNA based on its homology to previously cloned G-protein-coupled receptors. The rat receptor consists of 438 amino acids with seven transmembrane domains and is positively coupled to adenylyl cyclase via the Gs G-protein [Monsma, F. J. et al., *Mol. Pharmacol.* 1993, 43, 320-327]. Human 5-HT6 receptors, a 440 amino acid polypeptide, display 89% overall sequence homology with the rat receptors and is positively coupled to an adenylate cyclase second messenger system [Kohen, R. et al., *J. Neurochem.* 1996, 66, 47-56]. Rat and human 5-HT6 mRNA is located in the striatum, amygdala, nucleus accumbens, hippocampus, cortex and olfactory tubercle, but has not been found in peripheral organs studied. In pharmacological studies, tritiated 5-HT, tritiated LSD, and [$^{125}$I]-2-iodo LSD have been used to radiolabel 5-HT6 receptors. 5-HT binds with moderately high affinity (Ki=50-150 nM). Tricyclic antipsychotic agents and some antidepressants bind with significant affinity. A related investigation examined antipsychotics in greater detail and found that representative members of several classes of antipsychotics bind with high affinity. Examples include phenothiazine chlorpromazine, thioxanthene chlorprothixene, diphenylbutylpiperidine pimozide, heterocyclic antipsychotic agent loxapine and clozapine [Roth, B. L. et al., *J. Pharmacol. Exp. Ther.* 1994, 268, 1403-1410]. These results led to suggestions that 5-HT6 receptors might play a role in certain types of psychoses and that they might represent significant targets for the atypical antipsychotics in particular.

Until selective ligands were developed, exploration of 5-HT6 pharmacology was largely dependent on the use of nonselective agents. In the absence of selective ligands for the receptor, functional studies have been carried out using an antisense approach. 5-HT6 specific antisense produced a specific behavioural syndrome of yawning, stretching and chewing, but had no other discernable action in rats. The nonselective ligands were useful for investigating the pharmacology of 5-HT6 systems in preparations where other 5-HT receptors were absent (e.g., cAMP assays); however, owing to their lack of selectivity, they were of limited value for most other pharmacological studies.

Recent advent of selective agents has greatly benefited 5-HT6 studies, and this field of research has recently exploded. The development of more selective ligands may therefore lead to treatments with increased efficacy and reduced side effects. Alternatively, selective ligands may form completely novel therapies. It was not until 1998 that the first 5-HT6-selective antagonist was described, and this prompted others to quickly report their efforts in this area. Sleight et al. at Hoffman-La Roche Co. identified the bisaryl sulfonamides Ro 04-6790 (1, Ki=55 nM), Ro 63-0563 (2, Ki=12 nM) as very selective 5-HT6 antagonists [Sleight, A. J. et al., *Br. J. Pharmacol.* 1998, 124, 556-562]. Shortly thereafter, MS-245 (3, Ki=2.3 nM) was reported. Interestingly, although they represented independent discoveries, all three were identified by random screening methods and all three possess a sulfonamide moiety.

One problem associated with these antagonists was their low penetration of the CNS. At the time, Smith-Kline Beecham Co. also pinched out compound 4 via high-throughput screening. It displayed high affinity (Ki=5 nM) for 5-HT6 receptors and >50-fold selectivity over 10 other 5-HT receptors and no measurable affinity for 50 other receptor/binding sites. It was a pure antagonist of cAMP accumulation (pKb=7.8) [Bromidge, S. M. et al., *J. Med. Chem.* 1999, 42, 202-205]. It was moderately brain penetrant (25%) but subject to rapid blood clearance resulting in low bioavailability.

An ensuing structure activity study identified SB-271046 (5, Ki=1 nM; >200 selectivity over 50 other receptors) retained antagonist activity, and although less brain-penetrant (10%), it showed excellent (>80%) oral bioavailability.

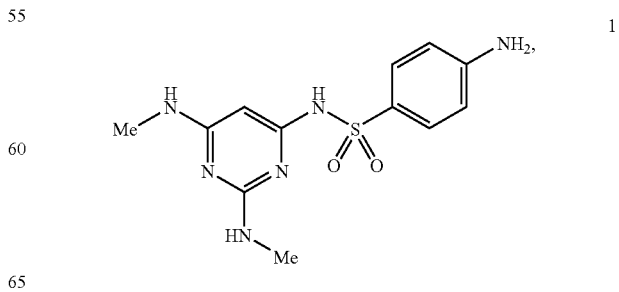

RO 04-6790

-continued

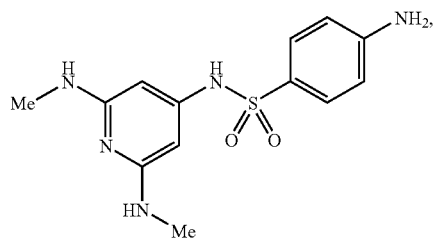

RO 63-0563

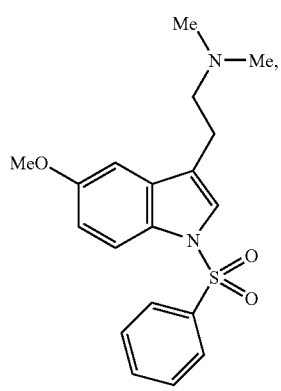

MS-245

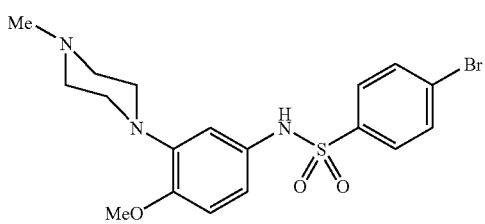

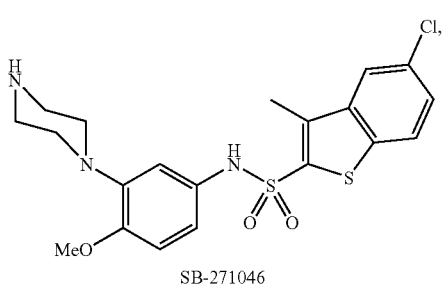

SB-271046

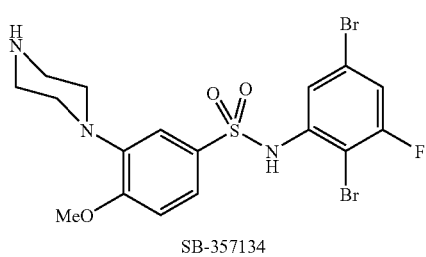

SB-357134

-continued

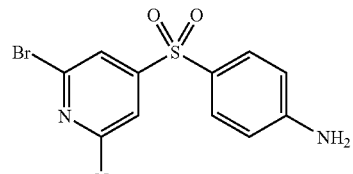

7

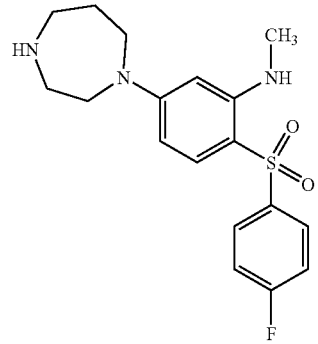

8

Subsequent studies by this group showed that SB-357134 (6, Ki=3 nM) with a low clearance rate and excellent oral bioavailability. In 1999, Glennon et al. undertook a structure affinity investigation of the binding of tryptamine derivatives at human 5-HT6 receptors [Glennon, R. A. et al., *J. Med. Chem.* 2000, 43, 1011-1018]. MS-245 was found as an antagonist (pA2=8.88) with high affinity (Ki=2.3 nM). In contrast to the above-mentioned sulfonamides or tryptamine derivatives, Hoffmann-LaRoche (7) and Pharmacia-Upjohn (8, Ki=1.4 nM) recently revealed several sulfones [Slassi, A. et al., *Expert Opin. Ther. Pat.* 2002, 12, 513-527]. Newer agents continue to be developed in attempts to improve pharmacokinetic and pharmacodynamic properties. Now that some tools are available, attention is focusing more and more on the function of 5-HT6 receptors.

A typical antipsychotics, in particular, display high affinity at these receptors (vide supra). In addition, the tritiated atypical antipsychotic agent [$^3$H]clozapine was shown to label two populations of receptors in rat brain and one population was thought to represent 5-HT6 receptors [Glatt, C. E. et al., *Mol. Med.* 1995, 1, 398-406]. Vogt et al. performed a systematic mutation scan of the coding region of the 5-HT6 receptor gene of 137 individuals (including schizophrenic and depressed patients) and concluded that the gene might be involved in bipolar affective disorder [Vogt, I. R. et al., *Am. J. Med. Genet.* 2000, 96, 217-221].

Prior to the identification of 5-HT6-selective agents, Bourson et al. demonstrated that intracerebroventricular administration of antisense oligonucleotides produced in rats a specific behavior of yawning, stretching, and chewing, which could be antagonized by atropine [Bourson, A. et al., *J. Pharmacol. Exp. Ther.* 1995, 274, 173-180]. Sleight et al. demonstrated that Ro 04-6790 (1) was capable of inducing this same effect. Owing to a relationship between cholinergic function and cognition, this led to speculation that 5-HT6 receptors might be involved in memory and cognitive dysfunction [Sleight, A. J. et al., *Neuropharmacology* 2001, 41, 210-219; Rogers, D. C. et al., *Psychopharmacology (Berlin)* 2001, 158, 114-119].

In addition, because antisense oligonucleotide pretreatment and Ro 04-6790 administration both led to decreased food intake by rats, it was suggested that 5-HT6 receptors might be involved in the regulation of feeding. Furthermore, Russell and Dias have questioned the postulate that 5-HT6 antagonists increase cholinergic transmission [Russell, M. G. N.; Dias, R., Curr. Top. Med. Chem. 2002, 2, 643-654].

Despite the mechanistic disagreement, there is evidence for the involvement of 5-HT6 receptors in learning and memory. When a water maze was used with rats as subjects, SB-271046 (5) and SB-357134 (6) showed significant improvement in retention of a previously learned task. Furthermore, SB-271046 (5) increased extracellular glutamate levels in frontal cortex and dorsal hippocampus by several fold, leading to the conclusion that selective enhancement of excitatory neurotransmission by SB-271046 supports a role for 5-HT6 receptor antagonists in the treatment of cognitive disorders and memory dysfunction [Dawson, L. A. et al., Neuropsychopharmacology 2001, 25, 662-668].

In addition, SB-357134 (6) produced a potent and dose-dependent increase in seizure threshold (rat maximal electroseizure threshold) following oral administration, suggesting possible therapeutic utility in convulsive disorders [Stean, T. O. et al., Pharmacol. Biochem. Behav. 2002, 71, 645-654]. These findings are consistent with an earlier finding that SB-271046 (5) and Ro 04-6790 (1) possess anticonvulsant activity.

Overall, there is some evidence to suggest that 5-HT6 receptors could be involved in psychosis. There is still more evidence that these receptors are involved in cognition and learning and additional evidence that they might have a role in convulsive disorders and appetite control. Although additional studies are certainly warranted, particularly with some of the newer 5-HT6 antagonists that are more brain-penetrant than the earlier agents, the future of 5-HT6 receptor ligands as potential therapeutic agents is quite exciting.

The inventors made an effort to develop a 5-HT6 antagonist having excellent binding affinity and selectivity, and has completed the present invention by discovering that quinoline-2,4-dione derivatives are 5-HT6 antagonists having very excellent binding strength and selectivity compared to sulfonamide or sulfonic structures disclosed in the prior art.

SUMMARY OF THE INVENTION

The present invention provides 3-aryl-3-methyl-quinoline-2,4-diones and a pharmaceutically acceptable salt thereof.

Additionally, the present invention provides a preparation method for 3-aryl-3-methyl-quinoline-2,4-diones.

Additionally, the present invention provides a pharmaceutical composition including 3-aryl-3-methyl-quinoline-2,4-diones for treatment of the central nervous system disorders.

DETAILED DESCRIPTION OF THE INVENTION

Figure 1:
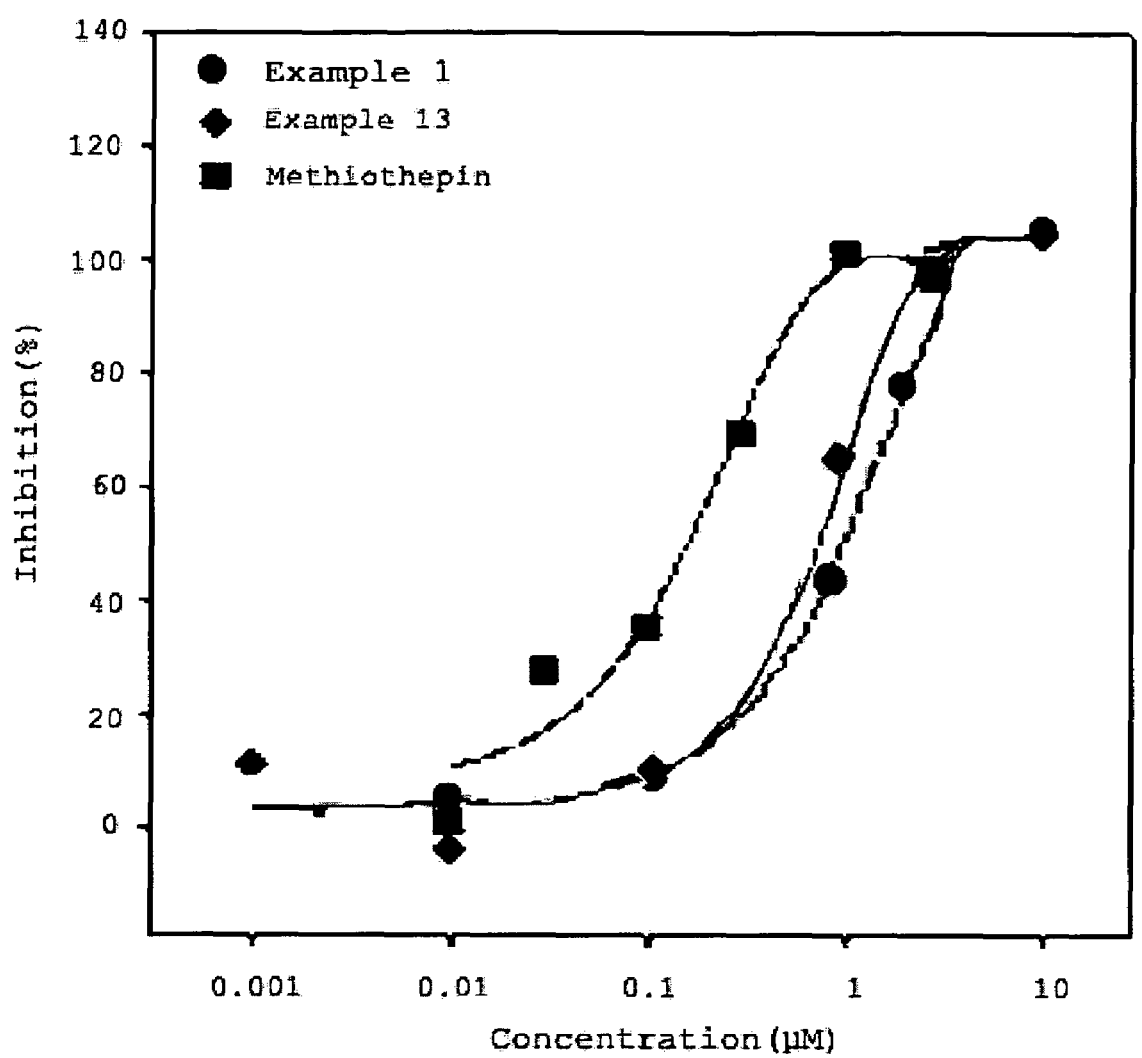
FIG. 1 is a graph showing an inhibitory effect of a compound of example 13 and methiothepin on cAMP accumulation mediated by 5-HT6 receptor of human HeLa cell.

The present invention provides 3-aryl-3-methyl-quinoline-2,4-diones represented by formula 1 or a pharmaceutically acceptable salt thereof.

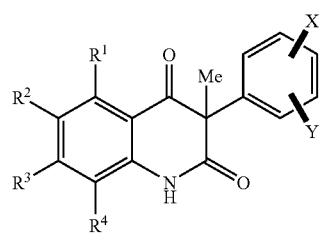

Formula 1 wherein, $R^1 \sim R^4$ are independently a hydrogen, hydroxyl, halogen, nitro, amino, C1-C4 haloalkyl, cyano, alkyl (C1~C4), alkenyl (C2~C4), alkynyl (C2~C4), azido, acylamino, aryl (C6·C14), alkoxy (C1~C4), aryloxy, benzyloxy, piperidinyl, N-methyl piperidinyl, or heterocyclic group; and X and Y are independently a hydrogen, halogen, nitro, amino, cyclic amino, piperazinyl, carboxyl, alkylsulfinyl, haloalkyl, cyano, alkyl, alkenyl, alkynyl, azido, acylamino, sulfonyl, aminosulfonyl, aryl, alkoxy, heterocyclic, acyloxy, alkylthionyl, arylthionyl, alkyloxycarbonyl, aryloxycarbonyl, aralkyloxycarbonyl, or, carbamoyl, ureido, or amidino group substituted by an alkyl (C1~C4), aryl (C6~C14), or aralkyl group.

Preferably, the $R^1 \sim R^4$ are independently a hydrogen, nitro, amino, chloro, bromo, alkoxy, or alkyl group; and X and Y are independently a hydrogen, chloro, bromo, fluoro, trifluoromethyl, nitro, amino, methoxy, hydroxy, or benzyloxy group.

In the above chemical compounds, the aryl group (C6~C14) includes a phenyl, naphthyl, phenanthryl, anthracyl, indenyl, azulenyl, biphenyl, biphenylenyl, and fluorenyl group.

The amino group includes —$NH_2$, —$NHR_5$, and —$NR_5R_6$, wherein $R_5$ and $R_6$ are independently an alkyl (C1~C4) group.

The halogen element includes fluorine, chlorine, bromine and iodine.

The alkyl (C1~C4) group includes a methyl, ethyl, propyl, isopropyl, butyl, secondary-butyl, and tertiary-butyl group.

The alkenyl (C2~C4) group includes a vinyl, aryl, 1-butenyl, 2-butenyl, 3-butenyl, and isobutenyl group.

The alkynyl (C2~C4) group includes a propargyl, 1-propynyl, 2-propynyl, 1-butynyl, 2-butynyl, and 3-butynyl group.

The haloalkyl group includes alkyl (C1~C4) group substituted by one or more fluorine, chlorine, bromine, or iodine, such as fluoromethyl, difluoromethyl, trifluoromethyl, pentafluoroethyl, 1,1-difluoroethyl, and trichloromethyl group.

The alkoxy (C1~C4) group includes oxygen substituted by one of the alkyl (C1~C4) groups.

The aralkyl group includes an alkyl (C1~C4) group substituted by an aryl (C6~C14) group.

The heterocyclic group includes heterocycloalkyl (C3~C7), heterocycloalkyl (C3~C7) alkyl (C1~C6), heteroaryl, and heteroaryl alkyl (C1~C6) group. The heterocycloalkyl group includes groups such as piperidyl, piperazinyl, and morpholidyl. The heteroaryl group includes groups such as pyridyl, quinolyl, isoquinolyl, pyridazinyl, pyrimidinyl, pyrazinyl, pyrolyl, indolyl, pyranyl, furyl, benzofuryl, thienyl, benzothienyl, imidazolyl, oxadiazolyl, thiazolyl, and thiadiazolyl.

More preferably, the compounds of formula 1 according to the present invention are selected from the group consisting of:

5,7-dichloro-3-methyl-3-phenyl-1H-quinoline-2,4-dione;
3-methyl-3-phenyl-1H-quinoline-2,4-dione;
7-chloro-3-methyl-3-phenyl-1H-quinoline-2,4-dione;
5,7-dibromo-3-methyl-3-phenyl-1H-quinoline-2,4-dione;
5-chloro-7-methoxy-3-methyl-3-phenyl-1H-quinoline-2,4-dione;
7-chloro-5-methoxy-3-methyl-3-phenyl-1H-quinoline-2,4-dione;
5-bromo-7-methoxy-3-methyl-3-phenyl-1H-quinoline-2,4-dione;
5,7-dimethoxy-3-methyl-3-phenyl-1H-quinoline-2,4-dione;
6,7-dichloro-3-methyl-3-phenyl-1H-quinoline-2,4-dione;
6,8-dibromo-3-methyl-3-phenyl-1H-quinoline-2,4-dione;
5-chloro-7-dimethylamino-3-methyl-3-phenyl-1H-quinoline-2,4-dione;
5,7-dichloro-3-(4-methoxy-phenyl)-3-methyl-1H-quinoline-2,4-dione;
5,7-dichloro-3-(4-hydroxy-phenyl)-3-methyl-1H-quinoline-2,4-dione;
5,7-dichloro-3-methyl-3-(4-nitro-phenyl)-1H-quinoline-2,4-dione;
3-(4-amino-phenyl)-5,7-dichloro-3-methyl-1H-quinoline-2,4-dione;
5,7-dichloro-3-(4-iodo-phenyl)-3-methyl-1H-quinoline-2,4-dione;
5,7-dichloro-3-(4-chloro-phenyl)-3-methyl-1H-quinoline-2,4-dione;
3-(4-bromo-phenyl)-5,7-dichloro-3-methyl-1H-quinoline-2,4-dione;
3-(3-benzyloxy-phenyl)-5,7-dichloro-3-methyl-1H-quinoline-2,4-dione;
3-(3-hydroxy-phenyl)-5,7-dichloro-3-methyl-1H-quinoline-2,4-dione;
5,7-dichloro-3-(4-methoxy-3-nitro-phenyl)-3-methyl-1H-quinoline-2,4-dione;
5,7-dichloro-3-(4-hydroxy-3-nitro-phenyl)-3-methyl-1H-quinoline-2,4-dione;
3-(4-benzyloxy-3-bromo-phenyl)-5,7-dichloro-3-methyl-1H-quinoline-2,4-dione;
3-(3-bromo-4-hydroxy-phenyl)-5,7-dichloro-3-methyl-1H-quinoline-2,4-dione;
3-[4-(1(S)-phenyl-ethyl-carbamoyl)-phenyl]-5,7-dichloro-3-methyl-1H-quinoline-2,4-dione;
3-[3-(1(S)-phenyl-ethyl-carbamoyl)-phenyl]-5,7-dichloro-3-methyl-1H-quinoline-2,4-dione;
3-(2,4-dibromo-phenyl)-5,7-dichloro-3-methyl-1H-quinoline-2,4-dione;
6,8-dibromo-3-(4-methoxy-3-nitro-phenyl)-3-methyl-1H-quinoline-2,4-dione;
3-(3-amino-4-methoxy-phenyl)-6,8-dibromo-3-methyl-1H-quinoline-2,4-dione;
3-(3-amino-4-hydroxy-phenyl)-6,8-dibromo-3-methyl-1H-quinoline-2,4-dione;
3-(4-hydroxy-3-methoxy-phenyl)-3-methyl-1H-quinoline-2,4-dione;
3-(3,4-dihydroxy-phenyl)-3-methyl-1H-quinoline-2,4-dione;
3-(4-methoxy-phenyl)-3-methyl-1H-quinoline-2,4-dione;
3-(4-hydroxy-phenyl)-3-methyl-1H-quinoline-2,4-dione;
5-chloro-7-methoxy-3-(4-methoxy-phenyl)-3-methyl-1H-quinoline-2,4-dione;
6,7-dichloro-3-methyl-3-(4-nitro-phenyl)-1H-quinoline-2,4-dione;
7-chloro-3-methyl-3-(4-nitro-phenyl)-1H-quinoline-2,4-dione;
3-(4-amino-phenyl)-7-chloro-3-methyl-1H-quinoline-2,4-dione;
5,7-dichloro-3-methyl-3-(4-methylamino-phenyl)-1H-quinoline-2,4-dione;
5,7-dichloro-3-(4-dimethylamino-phenyl)-3-methyl-1H-quinoline-2,4-dione;
5,7-dichloro-3-methyl-3-(4-ethylamino-phenyl)-1H-quinoline-2,4-dione;
5,7-dichloro-3-(4-diethylamino-phenyl)-3-methyl-1H-quinoline-2,4-dione;
1-(R)-[3-(5,7-dichloro-3-methyl-2,4-dioxo-1,2,3,4-tetrahydro-quinoline-3-yl)-phenyl]-3-(1-(S)-phenyl-ethyl)-urea;
1-(S)-[3-(5,7-dichloro-3-methyl-2,4-dioxo-1,2,3,4-tetrahydro-quinoline-3-yl)-phenyl]-3-(1-(S)-phenyl-ethyl)-urea;
7-chloro-3-(2,4-dibromo-phenyl)-3-methyl-1H-quinoline-2,4-dione;
5-chloro-3-(4-methoxy-phenyl)-3-methyl-7-(4-methyl-piperazine-1-yl)-1H-quinoline-2,4-dione;
5-chloro-3-(4-hydroxy-phenyl)-3-methyl-7-(4-methyl-piperazine-1-yl)-1H-quinoline-2,4-dione;
3-(4-amino-phenyl)-5-chloro-3-methyl-7-(4-methyl-piperazine-1-yl)-1H-quinoline-2,4-dione;
5-chloro-3-methyl-7-(4-methyl-piperazine-1-yl)-3-(4-nitro-phenyl)-1H-quinoline-2,4-dione;
3-(4-amino-phenyl)-3-methyl-7-(4-methyl-piperazine-1-yl)-1H-quinoline-2,4-dione;
3-methyl-7-(4-methyl-piperazine-1-yl)-3-(4-nitro-phenyl)-1H-quinoline-2,4-dione; and
3-(4-bromo-phenyl)-5-chloro-7-methoxy-3-methyl-1H-quinoline-2,4-dione.

However, the chemical compounds of formula 1 according to the present invention are not limited to the above-listed compounds.

Salts of the compounds of formula 1 according to the present invention should be a pharmaceutically accepted non-toxic salt in order to be used as a medicine, and other salts may be used for preparation of the compounds according to the present invention, or preparation of a pharmaceutically acceptable non-toxic salt thereof.

The pharmaceutically acceptable salts include alkali metal salts such as lithium, sodium or potassium salts; alkaline earth metal such as calcium or magnesium salts; and salts formed with suitable organic ligands such as quaternary ammonium salts. In the case of acid addition salt, for example, a solution of the compound according to the present invention may be mixed with pharmaceutically acceptable non-toxic acid solution such as hydrochloric acid, fumaric acid, maleic acid, succinic acid, acetic acid, citric acid, tartaric acid, carbonic acid or phosphoric acid.

The compounds according to the present invention include various tautomers of the compounds of formula 1.

In the case that the compounds of formula 1 according to the present invention have at least one asymmetric center, they may exist accordingly as optical isomers. In the case that the compounds of formula 1 according to the present invention have more than one asymmetric center, they may exist additionally as diastereomers. All the isomers of the compound according to the present invention and mixtures thereof are included in the scope of the present invention.

The compounds according to the present invention include prodrugs of the compounds of formula 1. Generally, such prodrugs will be functional derivatives of the compounds of formula 1 which are readily converted in vivo into the required compounds. The suitable prodrugs according to the present invention may be selected and prepared by a conventional method ("Design of Prodrugs", ed. H. Bundgaard, Elsevier, 1985).

Additionally, the present invention provides a preparation method of 3-aryl-3-methyl-quinoline-2,4-diones of formula 1.

The preparation method of 3-aryl-3-methyl-quinoline-2,4-diones includes the steps of: preparing the compound of formula 4 by a coupling reaction of the compounds of formula 2 and formula 3 in the presence of a proper coupling agent; and cyclizing the compound of formula 4 under proper basic condition.

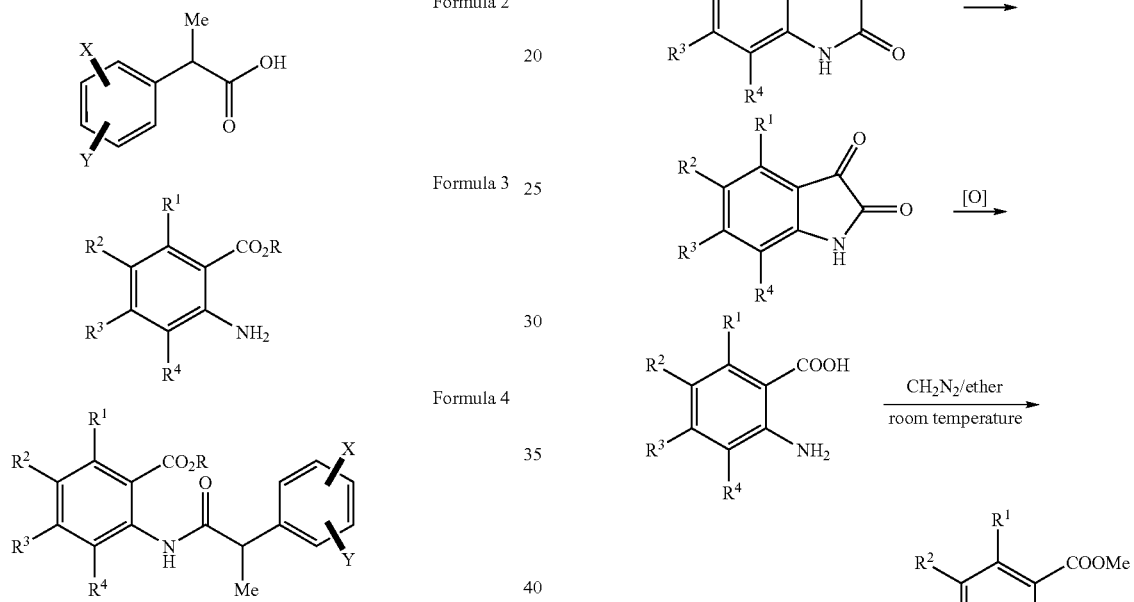

Formula 2

Formula 3

Formula 4

In the above formula 2, 3 and 4, the $R^1$~$R^4$, X and Y are same as the aforementioned definition in formula 1, and R is an alkyl (C1~C4) group. Preferably, the R is a methyl, ethyl, or propyl group.

Hereinafter, a preparation method for the 3-aryl-3-methyl-quinoline-2,4-diones according to the present invention will be described in detail.

The compound of formula 1 may be obtained by cyclization of an intermediate of formula 4. This reaction is performed under the presence of proper base, and is completed with mild acid. The proper base includes sodium metal, potassium metal, sodium hydride, lithium hexamethyldisilazide, and potassium hexamethyldisilazide.

The compound of formula 4 is obtained by a coupling reaction between a compound of formula 2 and a compound of formula 3. The reaction is performed in the steps of: 1) forming an acid chloride by reacting the compound of formula 2 with $SOCl_2$, $(COCl)_2$, $PCl_5$, or BOP-Cl (bis(2-oxo-diazolidinyl)phosphinic chloride) in an inert solvent such as dichloromethane or 1,2-dichloroethane; 2) coupling the acid chloride of a compound of formula 2 and a compound of formula 3 in an inert solvent by mixing and heating them.

The intermediate of formula 2 may conveniently be prepared by hydrolysis of the corresponding alkyl ester in aqueous sodium hydroxide solution or sodium hydroxide solution;

the anthranilic acid ester of formula 3 may be prepared by the procedures described in the reaction formular 1, or by the analogous procedures for known compounds in the art.

Reaction formula 1

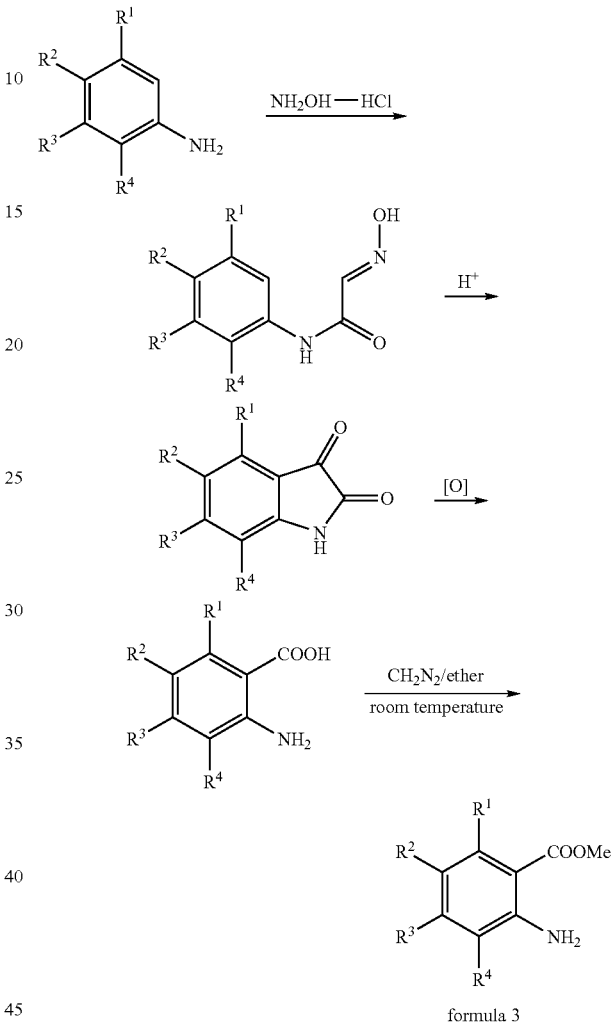

formula 3 in the above reaction formula 1, $R^1$~$R^4$, X, and Y are same as the aforementioned definition in chemical formula 1, R is an alkyl (C1~C4) group.

Where the above described processes for the preparation of the compounds according to the invention give rise to mixtures of stereoisomers, these isomers may be separated by conventional techniques such as preparative chromatography. The compounds may be prepared in racemic form, or individual enantiomers may be prepared either by asymmetric synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary. The present invention extends to cover all structural and optical isomers of the various compounds as well as racemic mixture thereof.

Additionally, the present invention provides a pharmaceutical composition of a 5-HT6 antagonist including the compound of formula 1 and pharmaceutically acceptable salts thereof.

The compound according to the present invention has excellent binding affinity to a serotonin 5-HT6 receptor (Refer to FIG. 1 and Table 2), excellent 5-HT6 receptor selectivity with respect to other receptors (Table 4), and an effect of inhibiting hyperactivity and stereotyped behavior in rats induced by methamphetamine (2 mg/kg, i.p.) (FIG. 2 and FIG. 3). Therefore, it may be effectively used as a 5-HT6 antagonist.

Accordingly, a pharmaceutical composition according to the present invention may be used for treatment 5-HT6 receptor related disorders of the central nervous system, and particularly for cognitive disorders, Alzheimer disease, anxiety, depression, schizophrenia, stress disorder, panic disorder, phobic disorder, obsessive compulsive disorder, post-traumatic-stress syndrome, psychosis, paraphrenia, mania, convulsive disorder, migraine, drug addition, obesity, eating disorder, or sleep disorder.

The compound according to the present invention may be supplied in various formulations such as oral or parenteral administration, or may be preferably administered by intravenous infusion. In pharmaceutical preparation, excipients and diluent such as a filler, bulking agent, binding agent, wetting agent, disintegrant, surfactant may generally be added. The pharmaceutical compositions of the present invention are preferably in unit dosage forms such as tablets, pills, capsules, powders, granules, sterile solutions or suspensions, or suppositories, for oral, intravenous, parenteral or rectal administration. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate. The liquid forms in which the novel compositions of the present invention may be incorporated for administration orally or by injection include aqueous solutions, syrups, aqueous or oil suspensions, and emulsions with edible oils such as cottonseed oil, sesame oil, coconut oil or peanut oil, as well as elixir and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

The preferable dosage level of the pharmaceutical composition of the present invention is about 0.01 to 250 mg/kg per day, preferably about 0.05 to 100 mg/kg per day, and especially about 0.05 to 5 mg/kg per day. The compounds may be administered on a regimen of 1 to 4 times per day. In a particular embodiment, the compounds may be conveniently administered by intravenous infusion.

Hereinafter, example embodiments of the present invention will be described in detail. Although the following preparation methods and examples are disclosed to illustrate the present invention, this invention should not be construed as limited to the following examples.

Preparation Example I (1) Intermediate I-1

N-(3,5-dichlorophenyl)-2-hydroxyimino-acetamide

A mixture of 3,5-dichloroaniline (10.0 g, 61.7 mmol) in water (50 mL), conc. HCl (12 mL), and 1,4-dioxane (20 mL) was heated until it becomes a clear solution. Subsequently, $CCl_3CHO.H_2O$ (chloral hydrate; 0.5 g, 66.9 mmol) and $Na_2SO_4$ (66.0 g) in water (224 mL), pre-warmed to 50° C., was added thereto. Subsequently, a solution of hydroxylamine hydrochloride (13.0 g, 180 mmol) in water (60 mL) was added to the mixture, and the reaction mixture was refluxed for 50 minutes with a reflux condenser. After cooling down the reaction mixture to room temperature, the insoluble solid was filtered, washed with excessive water, and dried in vacuo. Finally, the objective compound (12.8 g, 89%) was obtained as pale yellow solid: TLC $R_f$=0.5 (EtOAc:n-hexane=1:3); m.p. 196-197° C.; $^1$H NMR (DMSO-$d_6$) δ 7.39 (t, J=1.8 Hz, 1H, ArH), 7.70 (s, 1H, CHNOH), 7.89 (d, J=1.8 Hz, 2H, ArH), 10.54 (br s, 1H, NH), 12.40 (br s, 1H, NOH); MS(EI) m/e 233 [M$^+$], 216, 202, 189, 161.

2) Intermediate I-2

4,6-dichloro-1H-indole-2,3-dione

The Intermediate I-1 (10.0 g, 42.9 mmol) prepared by the above preparation example I(1) was slowly added to conc. sulfuric acid (50 mL) in an ice bath. At this moment, the temperature of the reaction mixture was maintained below 50° C. After complete the addition, the solution of dark color was heated for 10 minutes at 90° C. After cooling down the resultant to room temperature, the reactant was poured into ice having 10 times of the reactant volume, and was vigorously stirred for 1 hour. The insoluble solid formed in the above procedure was collected, washed with water, dried in vacuo, and the objective compound (8.90 g, 96%) was obtained as orange-colored solid: TLC $R_f$=0.4 (EtOAc:n-hexane=1:3); mp 228-230° C.; $^1$H NMR (DMSO-$d_6$) δ 6.97 (d, J=1.8 Hz, 1H, ArH), 7.32 (d, J=1.8 Hz, 1H, ArH), 11.42 (br s, 1H, NH); MS(EI) m/e 216 [M$^+$], 188 [M$^+$-$CO_2$], 160.

3) Intermediate I-3

2-amino-4,6-dichloro benzoic acid

At room temperature, to a solution of the intermediate I-2 (5.0 g, 23.1 mmol) prepared by the above preparation example I(2) in 75 mL 1N NaOH (aq) was added portionwise hydrogen peroxide (28% v/v, 10 mL). The reaction mixture was filtered after stirring for 2 hours to remove insoluble dark brown solid. The filterate was then carefully acidified to pH 2 by conc. hydrochloric acid. The formed yellow precipitates were collected, washed with water, and dried in vacuo. The objective compound (3.90 g, 82%) was obtained as ivory-colored solid by recrystallization from benzene: TLC $R_f$=0.1 (EtOAc:n-hexane=1:1); m.p. 188-189° C.; $^1$H NMR (DMSO-d$_6$) δ 6.76 (d, J=1.9 Hz, 1H, ArH), 6.85 (d, J=1.9 Hz, 1H, ArH); MS(EI) m/e 206 [M$^+$], 162 [M$^+$-CO$_2$].

4) Intermediate I-4

2-amino-4,6-dichlorobenzoic acid methyl ester

To a solution of the intermediate I-3 (11.5 g, 55.8 mmol) prepared by the above preparation example I(3) in 20 mL of ethyl ether was added dropwise Diazomethane ether solution (prepared from diazald in an ice bath; 1N solution 67.0 mL, 67.0 mmol). After complete the addition, the reaction mixture was warmed up to room temperature, and then agitation was continued until the intermediate I-3 was completely disappeared. In order to destroy unreacted diazomethane, acetic acid (6.87 mL, 120 mmol) was added to the mixture and the solvent was evaporated under reduced pressure, and an objective compound (12.1 g, quantitative yield) was obtained as orange-colored solid by solidifying yellow syrup formed therefrom in vacuo: $^1$H NMR (CDCl$_3$) δ 3.88 (s, 3H, OCH$_3$), 5.09 (br s, 2H, NH$_2$), 6.56 (d, J=1.8 Hz, 1H, ArH), 6.73 (d, J=1.8 Hz, 1H, ArH); MS(EI) m/e 219 [M$^+$], 190, 187.

5) Intermediate I-5

2-amino-4-chlorobenzoic acid methyl ester

The intermediate I-5 was prepared by the same procedure for the intermediate I-4 using a commercially available 2-amino-4-chlorobenzoic acid (20.0 g, 116.5 mmol). After normal workup, the objective compound was obtained as orange-colored solid (21.0 g, 97%): $^1$H NMR (200 MHz, CDCl$_3$) 53.84 (s, 3H, CO$_2$CH$_3$), 5.78 (br s, 2H, NH$_2$), 6.57 (dd, JA=2.0 Hz, JB=8.6 Hz, 1H, ArH), 6.64 (d, J=2.0 Hz, 1H, ArH), 7.75 (d, J=8.6 Hz, 1H, ArH); MS(EI) m/e 184 [M$^+$], 126.

6) Intermediate I-6

2-amino-4,5-dichloro-benzoic acid methyl ester

To a suspension of the intermediate I-5 (1.00 g, 5.39 mmol) in glacial acetic acid (10 mL) was added dropwise a solution of SOCl$_2$ (0.59 mL, 5.93 mmol) in glacial acetic acid (10 mL). The suspension was stirred for 3 hours at 30° C. After removing the solvent in vacuo and the residue was purified by chromatography on silica gel to give the objective compound (0.59 g, 50%): $^1$H NMR (200 MHz, CDCl$_3$) δ 3.86 (s, 3H), 5.76 (br s, 2H), 6.77 (s, 1H), 7.90 (s, 1H).

7) Intermediate I-7

2-amino-4,6-dibromo-benzoic acid methyl ester

To a solution of 2-amino-4,6-dibromo-benzoic acid (17.5 g, 59.3 mmol) in ether (150 mL) and ethyl acetate (15 mL) kept in an ice bath was added a solution of diazomethane (approximately 70.0 mmol, prepared from diazald 118.6 mmol) in ether (500 mL) over 1 hour. The reaction mixture was then stirred in an ice water bath for 2 hours. The resultant was treated with acetic acid 10 mL and washed with 2N NaHCO$_3$ and brine. The organic layer was concentrated in vacuo. The residue was purified by chromatography (hexane: EtOAc=8:1) to give the objective compound (15.3 g, 83%) as brown solid: $^1$H NMR (200 MHz, CDCl$_3$) δ 3.92 (s, 3H), 4.92 (br s, 2H), 6.80 (d, J=7.73, 2H), 7.11 (d, J=7.73, 1H); MS(EI) m/e 307 [M$^+$].

Preparation Example 1

Intermediate 1

4,6-dichloro-2-(2-phenyl-propionyl amino)-benzoic acid methyl ester

A mixture of 2-phenylpropionic acid (1.35 g, 9.00 mmol) and SOC$_2$ (2.34 mL, 27.0 mmol) in dichloromethane (15 mL) was stirred for 1 hour at room temperature, and refluxed overnight under a nitrogen atmosphere. The reaction mixture was cooled to room temperature, and concentrating the resulting solution under reduced pressure to obtain acid chloride as an intermediate. The acid chloride was then dissolved in dried CH$_2$Cl$_2$ (15 mL) without any additional purification. To the above solution was added dropwise a solution of 2-amino-4,6-dichloro-benzoic acid methyl ester (1.95 g, 8.88 mmol) in CH$_2$Cl$_2$(20 mL) at ice bath. After stirring for 30 minutes at 0° C., temperature was raised to room temperature and the stirring was continued overnight. The resultant was diluted with CH$_2$Cl$_2$ (50 mL) and washed with water (50 mL×2), brine (50 mL×2), and saturated NaHCO$_3$ solution, and dried over anhydrous sodium sulfate. After evaporation of the solvent, the residue was purified by a flash chromatography (hexane:EtOAc=10:1) to give the objective compound (2.88 g, 92%) as a pale yellow oil: $^1$H NMR (200 MHz, CDCl$_3$) δ 1.57 (d, J=7.0 Hz, 3H, CH$_3$), 3.75 (s, 3H, CO$_2$CH$_3$), 3.72-3.88 (m, 1H, CH), 7.10 (d, J=2.0 Hz, 1H, ArH), 7.24-7.41 (m, 5H, ArH), 8.38 (d, J=2.0 Hz, 1H, ArH), 8.97 (s, 1H, NH); MS(EI) m/e 353 [M$^+$+1], 320, 246, 105.

Preparation Example 2

Intermediate 2

2-(phenyl-propionylamino)-benzoic acid methyl ester

The objective compound was prepared by the same procedure for the intermediate 1, using a 2-phenyl-propionic acid (2.00 g, 13.3 mmol), SOCl$_2$ (2.88 mL, 40.0 mmol) and 2-amino benzoic acid methyl ester (1.40 g, 9.31 mmol). After normal workup, the pure objective compound (2.50 g, 95%) was obtained as a pale yellow syrup by a flash column chromatography (n-hexane:EtOAc=20:1): $^1$H NMR (200 MHz, CDCl$_3$) 51.60 (d, J=6.92 Hz, 3H, COCHCH$_3$), 3.72-3.87 (m, 4H, OCH$_3$, CH), 7.07 (td, J=6.10 Hz, 1.22 Hz, 1H, ArH), 7.23-7.55 (m, 6H, ArH), 7.95 (dd, J=7.73 Hz, 1.63 Hz, 1H, ArH), 8.69 (dd, J=8.55 Hz, 1.22 Hz, 1H, ArH).

Preparation Example 3

Intermediate 3

4-chloro-2-(2-phenyl-propionylamino)-benzoic acid methyl ester

The objective compound was prepared by the same procedure for the intermediate 1, using a 2-phenyl-propionic acid (2.00 g, 13.3 mmol), $SOCl_2$ (2.88 mL, 40.0 mmol) and 2-amino benzoic acid methyl ester (1.72 g, 9.31 mmol). After normal workup, the pure objective compound (2.43 g, 82%) was obtained as a pale yellow syrup by a flash column chromatography (n-hexane:EtOAc=20:1): $^1$H-NMR (200 MHz, $CDCl_3$) δ 1.61 (d, J=6.92 Hz, 3H, $CH_3$), 3.72-3.85 (m, 4H, $OCH_3$, CH), 6.95 (d, J=2.03 Hz, 1H, ArH), 6.99 (d, J=2.03 Hz, 1H, ArH), 7.24-7.45 (m, 5H, ArH), 7.84 (d, J=8.55 Hz, 1H, ArH), 8.84 (d, J=2.03 Hz, 1H, ArH), 11.15 (br s, 1H, NH).

Preparation Example 4

Intermediate 4

4,6-dibromo-2-(2-phenyl-propionylamino)-benzoic acid methyl ester

The objective compound was prepared by the same procedure for the intermediate 1, using a 2-phenyl-propionic acid (2.00 g, 13.3 mmol), $SOCl_2$ (3.47 mL, 40.0 mmol), and 2-amino-4,6-dibromo-benzoic acid methyl ester (2.74 g, 8.88 mmol). After normal workup, the pure objective compound (3.60 g, 92%) was obtained as white solid by a flash column chromatography (n-hexane:EtOAc=20:1): $^1$H NMR (200 MHz, $CDCl_3$) δ 1.60 (d, J=7.3 Hz, 3H, $CH_3$), 3.65-3.75 (m, 4H, $CO_2CH_3$ & CH) 7.24-7.44 (m, 5H, ArH), 7.48 (d, J=2.0 Hz, 1H, ArH), 8.55 (d, J=2.0 Hz, 1H, ArH), 8.68 (br s, 1H, NH).

Preparation Example 5

Intermediate 5

4,5-dichloro-2-(2-phenyl-propionylamino)-benzoic acid methyl ester

The objective compound was prepared by the same procedure for the intermediate 1, using a 2-phenyl-propionic acid (2.00 g, 13.3 mmol), $SOCl_2$ (2.28 mL, 40.0 mmol), and 2-amino-4,5-dichloro-benzoic acid methyl ester (1.95 g, 8.88 mmol). After normal workup, the pure objective compound (2.97 g, 95%) was obtained as pale yellow solid by a flash column chromatography (n-hexane:EtOAc=20:1): $^1$H NMR (200 MHz, $CDCl_3$) δ 1.59 (d, J=7.1 Hz, 3H, $CH_3$), 3.70-3.89 (m, 4H, $CO_2CH_3$ & CH), 7.28-7.42 (m, 5H, ArH), 8.03 (s, 1H, ArH), 8.99 (s, 1H, ArH), 11.00 (br s, 1H, NH).

Preparation Example 6

Intermediate 6

4,6-dichloro-2-[2-(4-methoxy-phenyl)-propionylamino]-benzoic acid methyl ester The objective compound was prepared by the same procedure for the intermediate 1, using a 2-(4-methoxy-phenyl)-propionic acid (1.45 g, 8.0 mmol), $SOCl_2$ (2.09 mL, 24.0 mmol), and 2-amino-4,6-dichloro-benzoic acid methyl ester (1.54 g, 7.0 mmol). After normal workup, the pure objective compound (2.27 g, 85%) was obtained as pale yellow syrup by a flash column chromatography (n-hexane:EtOAc=10:1): $^1$H NMR (200 MHz, $CDCl_3$) δ 1.56 (d, J=7.0 Hz, 3H, $CH_3$), 3.77 (s, 3H, $CO_2CH_3$), 3.81 (s, 3H, $OCH_3$), 3.84-3.95 (m, 1H, CH), 6.83-6.97 (m, 2H, ArH), 7.12 (d, J=2.0 Hz, 1H, ArH), 7.21-7.27 (m, 2H, ArH), 8.41 (d, J=2.0 Hz, 1H, ArH), 8.98 (s, 1H, NH); HRMS(EI) calcd. for $C_{18}H_{17}O_4NCl_2$ m/e 381.0536 [M$^+$], found 381.0539.

Preparation Example 7

Intermediate 7

4,6-dichloro-2-[2-(4-nitro-phenyl)-propionylamino]-benzoic acid methyl ester The objective compound was prepared by the same procedure for the intermediate 1, using a 2-(4-nitro-phenyl)-propionic acid (1.40 g, 7.17 mmol), $SOCl_2$ (5.1 mL, 71.7 mmol), and 2-amino-4,6-dichloro-benzoic acid methyl ester (1.6 g, 5.74 mmol). After normal workup, the pure objective compound (2.26 g, 99%) was obtained as pale yellow solid by recrystallization (ethyl acetate:ethyl ether=1:5): $^1$H NMR (200 MHz, $CDCl_3$) δ 1.63 (d, J=7.1 Hz, 3H, $CH_3$), 3.85-3.86 (m, 4H, $CO_2CH_3$ & CH), 7.18 (d, J=2.0 Hz, 1H, ArH), 7.54 (d, J=8.7 Hz, 2H, ArH), 8.24 (d, J=8.7 Hz, 2H, ArH), 8.45 (d, J=2.0 Hz, 1H, ArH), 9.59 (br s, 1H, ArH).

Preparation Example 8

Intermediate 8

2-[2-(4-bromo-phenyl)-propionylamino]-4,6-dichlorobenzoic acid methyl ester

The objective compound was prepared by the same procedure for the intermediate 1, using a 2-(4-bromo-phenyl)-propionic acid (11.7 g, 48.3 mmol), $SOCl_2$ (35.0 mL, 480 mmol), and 2-amino-4,6-dichloro-benzoic acid methyl ester (10.1 g, 45.9 mmol). After normal workup, the pure objective compound (9.31 g, 55%) was obtained as white solid by a flash column chromatography (n-hexane:EtOAc=10:1): $^1$H NMR (200 MHz, $CDCl_3$) δ 1.58 (d, J=7.1 Hz, 3H, $CH_3$), 3.75 (q, J=7.1 Hz, 1H, CH), 3.81 (s, 3H, $CO_2CH_3$), 7.15 (d, J=2.0 Hz, 1H, ArH), 7.20-7.53 (m, 4H, ArH), 8.41 (d, J=1.7 Hz, 1H, ArH), 9.16 (br s, 1H, NH).

Preparation Example 9

Intermediate 9

2-[2-(3-benzyloxy-phenyl)-propionylamino]-4,6-dichloro-benzoic acid methyl ester The objective compound was prepared by the same procedure for the intermediate 1, using a 2-(4-benzyloxy-phenyl)-propionic acid (2.70 g, 10.5 mmol), $PCl_5$ (2.30 g, 10.5 mmol), and 2-amino-4,6-dichloro-benzoic acid methyl ester (1.54 g, 7.0 mmol). After normal workup, the pure objective compound (2.90 g, 91%) was obtained as white solid by a flash column chromatography (n-hexane:EtOAc=10:1): $^1$H NMR (200 MHz, $CDCl_3$) δ 1.59 (d, J=7.0 Hz, 3H, $CH_3$), 3.65-3.76 (m, 1H, CH), 3.76 (s, 3H, $CO_2CH_3$), 5.09 (s, 2H, $OCH_2Ph$), 6.93-6.97 (m, 3H, ArH), 7.14 (d, J=1.8 Hz, 1H, ArH), 7.26-7.48 (m, 6H, ArH), 8.42 (d, J=1.8 Hz, 1H, ArH), 9.02 (s, 1H, NH); MS(EI) m/e 458 [M$_+$], 426, 336, 301, 121, 91.

Preparation Example 10

Intermediate 10

2-[2-(4-benzyloxy-3-bromo-phenyl)-propionylamino]-4,6-dichloro-benzoic acid methyl ester The objective compound was prepared by the same procedure for the intermediate 1, using a 2-(4-benzyloxy-3-bromophenyl)-propionic acid (1.0 g, 3.00 mmol), $SOCl_2$ (1.10 mL, 14.9 mmol), and 2-amino-4,6-dichloro-benzoic acid methyl ester (0.50 g, 2.40 mmol). After normal workup, the pure objective compound (0.91 g, 71%) was obtained as white solid by a flash column chromatography (n-hexane: EtOAc=5:1): $^1$H NMR (200 MHz, $CDCl_3$) δ 1.53 (s, 3H, $CH_3$), 3.62 (q, J=7.1 Hz, 1H, CH), 3.79 (s, 3H, $CO_2CH_3$), 5.16 (s, 2H, $CH_2Ph$), 6.94 (d, J=8.4 Hz, 1H, ArH), 7.15 (d, J=2.30 Hz, 1H, ArH), 7.20 (dd, J=8.6, 2.0 Hz, 1H, ArH), 7.31-7.48 (m, 5H, ArH), 7.54 (d, J=2.4 Hz, 1H, ArH), 8.41 (d, J=2.0 Hz, 1H, ArH), 9.15 (br s, 1H, NH).

Preparation Example 11

Intermediate 11

4,6-dichloro-2-[2-(4-methoxy-3-nitro-phenyl)-propionylamino]-benzoic acid methyl ester The objective compound was prepared by the same procedure for the intermediate 1, using a 2-(4-methoxy-3-nitro-phenyl)-propionic acid (0.60 g, 2.70 mmol), $SOC_2$ (0.96 mL, 13.0 mmol), and 2-amino-4,6-dichloro-benzoic acid methyl ester (0.77 g, 3.50 mmol). After normal workup, the pure objective compound (0.98 g, 82%) was obtained as white solid by recrystallization (dichloromethane:n-hexane=1:3): m.p 122° C.; $^1$H NMR (200 MHz, $CDCl_3$) δ 1.60 (d, J=7.2 Hz, 3H, $CH_3$), 3.65-3.84 (m, 4H, $CO_2CH_3$ & CH), 7.55 (dd, J=8.8, 2.2 Hz, 1H, ArH), 7.84 (d, J=2.2 Hz, 1H, ArH), 8.44 (d, J=2.0 Hz, 1H, ArH), 9.51 (br s, 1H, NH).

Preparation Example 12

Intermediate 12

4-chloro-2-[2-(4-nitro-phenyl)-propionylamino]-benzoic acid methyl ester

The objective compound was prepared by the same procedure for the intermediate 1, using a 2-(4-nitro-phenyl)-propionic acid (1.95 g, 10.0 mmol), $SOCl_2$ (3.6 mL, 33.4 mmol), and 2-amino-4-chloro-benzoic acid methyl ester (1.24 g, 6.67 mmol). After normal workup, the pure objective compound (2.29 g, 95%) was obtained as slightly yellow solid by a flash column chromatography (n-hexane:EtOAc=8:1): $^1$H NMR (200 MHz, $CDCl_3$) δ 1.65 (d, J=7.3 Hz, 3H, $CH_3$), 3.83-3.93 (m, 4H, $CO_2CH_3$ & CH), 7.04 (dd, J=8.5, 2.0 Hz, 1H, ArH), 7.58 (d, J=8.9 Hz, 2H, ArH), 7.93 (d, J=8.5 Hz, 1H, ArH), 8.21 (d, J=8.9 Hz, 2H, ArH), 8.79 (d, J=2.0 Hz, 1H, ArH), 11.09 (br s, 1H, NH).

Preparation Example 13

Intermediate 13

4,6-dibromo-2-[2-(4-methoxy-3-nitro-phenyl)-propionylamino]-benzoic acid methyl ester The objective compound was prepared by the same procedure for the intermediate 1, using a 2-(4-methoxy-3-nitro-phenyl)-propionic acid (0.22 g, 0.98 mmol), $SOCl_2$ (0.35 mL, 0.49 mmol), and 2-amino-4,6-dibromo-benzoic acid methyl ester (0.15 g, 0.49 mmol). After normal workup, the pure objective compound (0.15 g, 59%) was obtained as pale yellow solid by a flash column chromatography (n-hexane: EtOAc=3:1): $^1$H NMR (200 MHz, DMSO-$d_6$) δ 1.39 (d, J=6.8 Hz, 3H, $CH_3$), 3.55 (s, 3H, $OCH_3$), 3.88 (s, 3H, $CO_2CH_3$), 3.89 (m, 1H, CH), 7.32 (d, J=9.0 Hz, 1H, ArH), 7.63 (dd, J=8.8, 1.8 Hz, 1H, ArH), 7.80-7.84 (m, 2H, ArH), 8.13-8.15 (m, 1H, ArH).

Preparation Example 14

Intermediate 14

2-[2-(4-hydroxy-3-methoxy-phenyl)-propionylamino]-benzoic acid methyl ester The objective compound was prepared by the same procedure for the intermediate 1, using a 2-(4-hydroxy-3-methoxy-phenyl)-propionic acid (1.08 g, 5.50 mmol), $SOCl_2$ (1.20 mL, 16.6 mmol), and 2-amino-benzoic acid methyl ester (0.56 g, 3.7 mmol). After normal workup, the pure objective compound (1.02 g, 56%) was obtained as pale yellow syrup by a flash column chromatography (n-hexane:EtOAc=10:1): $^1$H NMR (200 MHz, $CDCl_3$) δ 1.57 (d, J=7.32 Hz, 3H, $CH_3$), 3.72 (q, J=7.32 Hz, 1H, CH), 3.85 (s, 3H, $OCH_3$), 3.88 (s, 3H, $COOCH_3$), 5.73 (br s, 1H, ArOH), 6.89-7.05 (m, 4H, ArH), 7.45 (t, J=8.55 Hz, 1H, ArH), 7.94 (d, J=7.73 Hz, 1H, ArH), 8.67 (d, J=8.55 Hz, 1H, ArH), 11.07 (br s, 1H, NH).

Preparation Example 15

Intermediate 15

2-[2-(4-methoxy-phenyl)-propionylamino]-benzoic acid methyl ester

The objective compound was prepared by the same procedure for the intermediate 1, using a 2-(4-methoxy-phenyl)-propionic acid (1.00 g, 5.55 mmol), $SOCl_2$ (1.20 mL, 16.6 mmol), and 2-amino-benzoic acid methyl (0.56 g, 3.7 mmol). After normal workup, the pure objective compound (1.63 g, 94%) was obtained of slightly yellow syrup by a flash column chromatography (n-hexane:EtOAc=10:1): $^1$H NMR (200 MHz, $CDCl_3$) δ 1.57 (d, J=6.91 Hz, 3H, $CH_3$), 3.67 3.79 (m, 4H, $CO_2CH_3$ & CH), 3.87 (s, 3H, $OCH_3$), 6.87-6.99 (m, 3H, ArH), 7.32-7.94 (m, 4H, ArH), 8.69 (d, J=8.6 Hz, 1H, ArH), 11.06 (br s, 1H, NH).

Example 1

5,7-dichloro-3-methyl-3-phenyl-1H-quinoline-2,4-dione

To a pre-cooled (−78° C.) solution of 4,6-dichloro-2-(2-phenyl-propionyl amino)-benzoic acid methyl ester (0.82 g, 2.30 mmol) in dry THF (70 mL) was added dropwise LiHMDS [prepared by treatment of a hexamethyldisilazide (1.47 mL, 6.90 mmol) in dry THF (25 mL) with n-BuLi (3.70 mmol, 2.5M hexane solution) for 1 hour at −78° C.]. The reaction mixture was stirred for 1 hour and then refluxed overnight under a nitrogen atmosphere. After cooling to room temperature, the reaction was quenched by the addition of 1N HCl aqueous solution. Subsequently, the resultant was extracted with ethyl acetate (150 mL×3), and organic phase was washed with brine (150 mL×2) and water (150 mL×2)

dried with magnesium sulfate. After evaporation the solvent, an objective compound (0.57 g, 78%) was obtained as yellow solid by a flash column chromatography (Hexane:EtOAc=4:1): $^1$H NMR (200 MHz, CD$_3$OD+DMSO-d$_6$) δ 1.61 (s, 3H, CH$_3$), 6.96 (m, 1H, ArH), 7.08-7.34 (m, 6H, ArH); m.p. 222-225° C.; MS(EI) m/e 319 [M$^+$], 285, 132, 104.

Example 2

3-methyl-3-phenyl-1H-quinoline-2,4-dione

The objective compound was prepared by the same procedure for the example 1, using a 2-(2-phenyl-propionyl amino)-benzoic acid methyl ester (1.00 g, 3.53 mmol) and LiHMDS (10.6 mmol, 1M THF solution). After normal workup, the pure objective compound (0.58 g, 65%) was obtained as pale yellow solid by a flash column chromatography (Hex:EtOAc=4:1): $^1$H NMR (200 MHz, CDCl$_3$) δ 2.05 (s, 3H, CH$_3$), 6.92 (d, J=8.14 Hz, 1H, ArH), 7.11 (t, J=7.73 Hz, 1H, ArH), 7.23-7.37 (m, 5H, ArH), 7.49 (t, J=7.32, 1H, ArH), 7.89 (d, J=7.73 Hz, 1H, ArH), 9.50 (br s, 1H, NH); m.p. 194-196° C.; MS(EI) m/e 251 [M$^+$], 146, 132, 104; HRMS m/e cacld. for C$_{16}$H$_{13}$NO$_2$ 251.0946, found 251.0944.

Example 3

7-chloro-3-methyl-3-phenyl-1H-quinoline-2,4-dione

The objective compound was prepared by the same procedure for the example 1, using a 4-chloro-2-(2-phenyl-propionyl amino)-benzoic acid methyl ester (1.00 g, 3.15 mmol) and LiHMDS (9.44 mmol, 1M solution in THF). After normal workup, the pure objective compound (0.54 g, 60%) was obtained as pale yellow solid by a flash column chromatography (Hex:EtOAc=4:1): $^1$H NMR (200 MHz, CDCl$_3$) δ 1.86 (s, 3H, CH$_3$), 6.94 (d, J=1.63 Hz, 1H, ArH), 7.06 (dd, J=8.55 Hz, 1.63 Hz, 1H, ArH), 7.26-7.32 (m, 5H, ArH), 7.83 (d, J=8.14 Hz, 1H, ArH), 9.21 (br s, 1H, NH); m.p. 174-175° C.; MS(EI) m/e 285 [M$^+$], 153, 132, 104; HRMS m/e cacld. for C$_{16}$H$_{12}$NO$_2$Cl 285.0557, found 285.0552.

Example 4

5,7-dibromo-3-methyl-3-phenyl-1H-quinoline-2,4-dione

The objective compound was prepared by the same procedure for the example 1, using a 4,6-dibromo-2-(2-phenyl-propionyl amino)-benzoic acid methyl ester (1.00 g, 2.27 mmol) and LiHMDS (6.81 mmol, 1M THF solution). After normal workup, the pure objective compound (0.60 g, 65%) was obtained as yellow solid by a flash column chromatography (Hex:EtOAc=4:1): $^1$H NMR (200 MHz, CDCl$_3$) δ 1.64 (s, 3H, CH$_3$), 7.04 (d, J=1.6 Hz, 1H, ArH), 7.17-7.37 (m, 5H, ArH), 7.46 (d, J=1.6 Hz, 1H, ArH), 9.35 (br s, 1H, NH); m.p. 202-203° C.; MS(EI) m/e 409 [M$^+$], 288, 132, 104; HRMS m/e cacld. for C$_{16}$H$_{11}$Br$_2$NO$_2$ 406.9157, found 406.9161.

Example 5

5-chloro-7-methoxy-3-methyl-3-phenyl-1H-quinoline-2,4-dione

Example 6

7-chloro-5-methoxy-3-methyl-3-phenyl-1H-quinoline-2,4-dione

To a solution of 5,7-dichloro-3-methyl-3-phenyl-1H-quinoline-2,4-dione (1.00 g, 3.12 mmol) in methanol (10 mL) was added NaOMe (0.67 g, 12.5 mmol) at room temperature. The reaction mixture was then heated for 10 hours at reflux temperature. After the reaction completion, the solvent was removed under reduced pressure. The residue was diluted with 1N HCl solution, and extracted with ethyl acetate (100 mL×3). Subsequently, the organic phase was dried over magnesium sulfate and concentrated in vacuo. The crude was purified by column chromatography (Hex:EtOAc=2:1) on silica gel to give the example 5 (0.40 g, 40%) and the example 6 (0.1 g, 10%):

example 5; $^1$H NMR (200 MHz, CDCl$_3$) δ 1.75 (s, 3H, CH$_3$), 3.90 (s, 3H, OCH$_3$), 6.47 (d, J=1.63 Hz, 1H, ArH), 6.57 (d, J=1.63 Hz, 1H, ArH), 7.26 (m, 5H, ArH), 8.78 (br s, 1H, NH); m.p. 256-257° C.; MS(EI) m/e 315 [M$^+$+1], 183, 132, 103; HRMS m/e cacld. for C$_{17}$H$_{14}$NO$_3$Cl 315.0662, found 315.0659.

example 6; $^1$H NMR (200 MHz, CDCl$_3$+CD$_3$OD) δ 1.76 (s, 3H, CH$_3$), 3.88 (s, 3H, OCH$_3$), 6.54 (d, J=1.63 Hz, 1H, ArH), 6.57 (d, J=1.63 Hz, 1H, ArH), 7.23 (m, 5H, ArH); m.p. 267-269° C.; MS(EI) m/e 314 [M$^+$], 184; HRMS m/e cacld. for C$_{17}$H$_{14}$NO$_3$Cl 315.0662, found 315.0672.

Example 7

5-bromo-7-methoxy-3-methyl-3-phenyl-1H-quinoline-2,4-dione

Example 8

5,7-dimethoxy-3-methyl-3-phenyl-1H-quinoline-2,4-dione

To a solution of 5,7-dibromo-3-methyl-3-phenyl-1H-quinoline-2,4-diones (1.00 g, 2.44 mmol) in methanol (10 mL) was added NaOMe (2.44 mmol) at room temperature. The reaction mixture was heated for 10 hours with a reflux condenser. After the reaction completion, the reaction mixture was poured into 1N HCl aqueous solution (100 mL). Resultant was extracted with ethyl acetate (100 mL×3), and organic phase was washed with brine (100 mL) and water (150 mL×2), dried over magnesium sulfate. After evaporation the solvent, the residue was purified by a flash column chromatography to give two objective compounds, example 7 (0.18 g, 20%, yellow solid), example 8 (0.24 g, 32%, yellow solid):

Example 7; $^1$H NMR (200 MHz, CDCl$_3$) δ 1.73 (s, 3H, CH$_3$), 3.90 (s, 3H, OCH$_3$), 6.59 (d, J=1.6 Hz, 1H, ArH), 6.72 (d, J=1.6 Hz, 1H, ArH), 7.25-7.28 (m, 5H, ArH), 8.33 (br s, 1H, NH); m.p. 193-195° C.; HRMS m/e cacld. for C$_{17}$H$_{14}$NO$_3$Br 359.0157, found 359.0156. 359.

Example 8; $^1$H NMR (200 MHz, CDCl$_3$) δ 1.77 (s, 3H, CH$_3$), 3.80 (s, 3H, OCH$_3$), 3.87 (s, 3H, OCH$_3$), 5.94 (d, J=2.0 Hz, 1H, ArH), 6.10 (d, J=2.0 Hz, 1H, ArH), 7.20-7.34 (m, 5H, ArH), 8.82 (br s, 1H, NH); m.p. 233-234° C.

Example 9

6,7-dichloro-3-methyl-3-phenyl-1H-quinoline-2,4-dione

The objective compound was prepared by the same procedure for the example 1, using a 4,5-dichloro-2-(2-phenyl-propionyl amino)-benzoic acid methyl ester (1.00 g, 2.84 mmol) and LiHMDS (8.52 mmol, 1M solution in THF). After normal workup, the pure objective compound (0.36 g, 40%; yellow solid) was obtained by a flash column chromatography (Hex:EtOAc=4:1): $^1$H NMR (200 MHz, CDCl$_3$) δ 1.83 (s, 3H, CH$_3$), 7.02 (s, 1H, ArH), 7.23-7.33 (m, 5H, ArH), 7.97 (s, 1H, ArH), 8.41 (br s, 1H, NH); m.p. 213-214° C.; MS(EI) m/e 319 [M$^+$], 285, 132, 104 ; HRMS m/e cacld. for C$_{16}$H$_{11}$NO$_2$Cl 319.0167, found 319.0168.

Example 10

6,8-dibromo-3-methyl-3-phenyl-1H-quinoline-2,14-dione

The objective compound was prepared by the same procedure for the example 1, using a 3,5-dibromo-2-(2-phenyl-propionyl amino)-benzoic acid methyl ester (1.00 g, 2.27 mmol) and LiHMDS (6.81 mmol, 1M solution in THF). After normal workup, the pure objective compound (0.33 g, 35%) was obtained as yellow solid by a flash column chromatography (Hex:EtOAc=4:1): $^1$H NMR (200 MHz, CDCl$_3$) δ 1.63 (s, 3H, CH$_3$), 6.45 (d, J=2.2 Hz, 1H, ArH), 7.12-7.34 (m, 5H, ArH), 7.67 (d, J=2.2 Hz, 1H, ArH), 9.35 (br s, 1H, NH); MS(EI) m/e 408 [M$^+$+1], 406 [M$^+$−1].

Example 11

5-chloro-7-dimethylamino-3-methyl-3-phenyl-1H-quinoline-2,4-dione

To a solution of 5,7-dichloro-3-methyl-3-phenyl-1H-quinoline-2,4-dione (1.00 g, 3.12 mmol) in MeCN (10 mL) were added K$_2$CO$_3$ (0.65 g, 4.68 mmol), triethylamine (0.65 mL, 4.68 mmol), and dimethylamine hydrochloride (0.35 g, 7.80 mmol) at room temperature. The reaction mixture was then heated for 10 hours at reflux temperature. After the reaction completed, the solvent was removed. The residue was diluted with 1N HCl solution and extracted with ethyl acetate (100 mL×2). The organic phase was dried over magnesium sulfate and concentrated in vacuo. The crude was purified by a column chromatography on silica gel to give the objective compound (0.67 g, 65%): $^1$H NMR (200 MHz, CDCl$_3$) δ 1.89 (s, 3H, CH$_3$), 2.64 (s, 6H, 2NCH$_3$), 6.29 (d, J=2.03 Hz, 1H, ArH), 6.49 (d, J=2.03 Hz, 1H, ArH), 7.23-7.33 (m, 5H, ArH), 9.13 (br s, 1H, NH); m.p. 224-226° C.; MS(EI) m/e 328 [M$^+$], 313, 196, 132; HRMS m/e cacld. for C$_{18}$H$_{17}$N$_2$O$_2$Cl 328.0979, found 328.0979.

Example 12

5,7-dichloro-3-(4-methoxy-phenyl)-3-methyl-1H-quinoline-2,4-dione

The objective compound was prepared by the same procedure for the example 1, using a 4,6-dichloro-2-[2-(4-methoxy-phenyl)-propionylamino]-benzoic acid methyl ester (1.44 g, 3.77 mmol) and LiHMDS (11.0 mmol, 1M solution in THF). After normal workup, the pure objective compound (0.55 g, 42%) was obtained as yellow solid by a flash column chromatography (n-hexane:EtOAc=10:1): $^1$H NMR (200 MHz, CDCl$_3$) δ 1.52 (s, 3H, CH$_3$), 3.67 (s, 3H, CO$_2$CH$_3$), 6.89 (d, J=8.9 Hz, 2H, ArH), 6.99-7.08 (m, 3H, ArH), 7.23 (d, J=1.9 Hz, 1H, ArH), 11.25 (s, 1H, NH); m.p. 210-212° C.; MS(EI) m/e 349 [M$^+$], 162, 134; HRMS m/e cacld. for C$_{17}$H$_{13}$NO$_3$Cl$_2$ 349.0272, found 349.0278.

Example 13

5,7-dichloro-3-(4-hydroxy-phenyl)-3-methyl-1H-quinoline-2,4-dione

To a pre-cooled (−78° C.) solution of 5,7-dichloro-3-(4-methoxy-phenyl)-3-methyl-1H-quinoline-2,4-dione (0.23 g, 0.77 mmol) in dichloromethane (5.0 mL) was added BBr$_3$ (1.40 mL, 1.0 M dichloromethane solution) by syringe. The reaction was conducted for 20 hours at room temperature and qeunched by carefully addition of 1N HCl aqueous solution. Resultant was extracted with ethyl acetate (50 mL×2), washed with brine (50 mL) and water (50 mL×2), and dried over magnesium sulfate. After concentration of the organic phase, the residue was subjected to purify by a flash column chromatography (n-hexane:EtOAc=5:1) to give a pure objective compound (0.19 g, 83%) as yellow solid: $^1$H NMR (300 MHz, CD$_3$OD) δ 1.58 (s, 3H, CH$_3$), 6.65-6.71 (m, 2H, ArH), 6.91 (d, J=1.9 Hz, 1H, ArH), 6.94-6.99 (m, 2H, ArH), 7.03-7.06 (m, 1H, ArH); m.p. 222-223° C.; MS(EI) m/e 335 [M$^+$], 188, 140, 120; HRMS m/e cacld. for C$_{16}$H$_{11}$NO$_3$Cl$_2$ 335.0116, found 335.0112.

Example 14

5,7-dichloro-3-methyl-3-(4-nitro-phenyl)-1H-quinoline-2,4-dione

To a suspension of sodium hydride (50 mg, 1.25 mmol, 60% in mineral oil) in dry THF (20 mL) was added a solution of 4,6-dichloro-2-[2-(4-nitro-phenyl)-propionylamino]-benzoic acid methyl ester (0.20 g, 0.50 mmol) in THF anhydride (5 mL) at 0° C. The reactant was stirred for 5 hours, and the reaction was quenched by addition of 0.5M HCl solution (30 mL). The resultant was extracted with ethyl acetate (50 mL×3), washed with water (50 mL×2) and brine (50 ml×2) and dried over magnesium sulfate anhydride. After evaporation of solvent, the pure objective compound (0.18 g, 99%) was obtained as pale yellow solid by a recrystallization (dichloromethane:EtOAc 3:1): $^1$H NMR (200 MHz, CDCl$_3$) δ 1.79 (s, 3H, CH$_3$), 6.80 (d, J=1.8 Hz, 1H, ArH), 7.15 (d, J=1.8 Hz, 1H, ArH), 7.38 (d, J=9.0 Hz, 2H, ArH), 8.18 (d, J=9.0 Hz, 2H), 8.43 (s, 1H, NH); MS(EI) m/e 364 [M$^+$].

Example 15

3-(4-amino-phenyl)-5,7-dichloro-3-methyl-1H-quinoline-2,4-dione

To a solution of 5,7-dichloro-3-methyl-3-(4-nitro-phenyl)-1H-quinoline-2,4-dione (1.0 g, 2.74 mmol) in methanol (30 mL) was added SnCl$_2$-2H$_2$O (1.85 g, 8.22 mmol). The resulting solution was stirred at reflux temperature overnight. After the reaction was completed, a yellow residue was obtained after evaporating solvent under reduced pressure. The residue was then diluted with 1N HCl solution (200 mL), and extracted with ethyl acetate (200 mL×3). The combined organic layer was washed with brine (200 ml×2) and water (200 mL×2) and dried over magnesium sulfate anhydride. After evaporation of the solvent, the objective compound (0.61 g, 66%) was obtained as pale yellow solid by purifying the residue with flash column chromatography (n-hexane: ethyl acetate=4:1): $^1$H NMR (200 MHz, CDCl$_3$) δ 1.68 (s, 3H, CH$_3$), 3.68 (br s, 2H, NH$_2$), 6.58 (d, J=8.8 Hz, 2H, ArH), 6.73 (d, J=1.8 Hz, 1H, ArH), 6.96 (d, J=8.8 Hz, 2H, ArH), 7.08 (d, J=1.8 Hz, 1H, ArH), 8.21 (br s, 1H, NH); MS(EI) m/e 335 [M$^+$+1].

Example 16

5,7-dichloro-3-(4-iodo-phenyl)-3-methyl-1H-quinoline-2,4-dione

To a solution of 3-(4-amino-phenyl)-5,7-dichloro-3-methyl-1H-quinoline-2,4-dione (84 mg, 0.25 mmol) in dry acetonitrile (10 mL) was added t-BuONO (50 μl, 0.38 mmol) at 0° C. After stirring for 15 minutes, $CuI_2$ (119 mg, 0.63 mmol) was added thereto, and the reaction solution was allowed to reach room temperature, and then was refluxed additionally for 30 minutes. The resulting suspension was poured into ice water (100 mL) and extracted with ethyl acetate (100 mL×3). The organic layers was washed with water (100 mL) and brine (100 ml×2), dried over anhydrous magnesium sulfate and concentrated in vacuo. The objective compound (42 mg, 38%) was obtained as white solid by a flash column chromatography (n-hexane:ethyl acetate=5:1): $^1$H NMR (200 MHz, $CDCl_3$) δ 1.72 (s, 3H, $CH_3$), 6.77 (d, J=1.8 Hz, 1H, ArH), 6.91-6.97 (m, 2H, ArH), 7.12 (d, J=1.8 Hz, 1H, ArH), 7.61-7.68 (m, 2H, ArH), 8.37 (br s, 1H, NH); MS(EI) m/e 445 [M$^+$], 258, 230, 103.

Example 17

5,7-dichloro-3-(4-chloro-phenyl)-3-methyl-1H-quinoline-2,4-dione

The objective compound was prepared by the same procedure for the example 16, using a 3-(4-amino-phenyl)-5,7-dichloro-3-methyl-1H-quinoline-2,4-dione (168 mg, 0.50 mmol), t-BuONO (100 μl, 0.75 mmol), and $CuCl_2$ (168 mg, 1.25 mmol). After normal workup, the objective compound (91 mg, 52%) was obtained as white solid by a flash column chromatography (n-hexane:EtOAc=5:1): $^1$H NMR (200 MHz, $CDCl_3$) δ 1.73 (s, 3H, $CH_3$), 6.81 (d, J=1.8 Hz, 1H, ArH), 7.11-7.30 (m, 5H, ArH), 8.82 (br s, 1H, NH); MS(EI) m/e 353 [M$^+$], 318, 187, 166, 138.

Example 18

3-(4-bromo-phenyl)-5,7-dichloro-3-methyl-1H-quinoline-2,4-dione

The objective compound was prepared by the same procedure for the example 1, using a 2-[2-(4-bromo-phenyl)-propionyl amino]-4,6-dichloro-benzoic acid methyl ester (400 mg, 0.93 mmol) and NaH (78 mg, 1.95 mmol) as a base instead of LiHMDS. After normal workup, the objective compound (60 mg, 18%) was obtained as white solid by a flash column chromatography (n-hexane:EtOAc=5:1): $^1$H NMR (200 MHz, $CDCl_3+CD_3OD$) δ 1.69 (s, 3H, $CH_3$), 6.91-7.48 (m, 6H, ArH); m.p. 237-238° C.; MS(EI) m/e 397 [M$^+$].

Example 19

3-(3-benzyloxy-phenyl)-5,7-dichloro-3-methyl-1H-quinoline-2,4-dione

The objective compound was prepared by the same procedure for the example 1, using a 4,6-dichloro-2-[2-(3-benzyloxy-phenyl)-propionylamino]-benzoic acid methyl ester (2.80 g, 6.40 mmol) and LiHMDS (19.0 mmol, 1M THF solution). After normal workup, the objective compound (1.90 g, 71%) was obtained as pale yellow solid by a flash column chromatography (n-hexane:EtOAc=9:1): $^1$H NMR (200 MHz, DMSO-$d_6$) δ 1.55 (s, 3H, $CH_3$), 5.02 (s, 2H, $OCH_2$), 6.69-7.02 (m, 2H, ArH), 7.22-7.38 (m, 7H, ArH), 11.28 (br s, 1H, NH); m.p. 201-203° C.; MS(EI) m/e 426 [M$^+$+1], 160, 91.

Example 20

3-(3-hydroxy-phenyl)-5,7-dichloro-3-methyl-1H-quinoline-2,4-dione

The objective compound was prepared by the same procedure for the example 13, using a 3-(3-benzyloxy-phenyl)-5,7-dichloro-3-methyl-1H-quinoline-2,4-dione (0.26 g, 0.60 mmol) and $BBr_3$ (1.20 mL, 1.0 M dichloromethane solution). After normal workup, the objective compound (0.18 g, 90%) was obtained as yellow solid by a flash column chromatography (n-hexane:EtOAc=5:1): $^1$H NMR (200 MHz, $CDCl_3$+DMSO-$d_6$) δ 1.62 (s, 3H, $CH_3$), 6.57-6.71 (m, 3H, ArH), 6.98-7.12 (m, 3H, ArH), 9.17 (s, 1H, OH), 11.07 (s, 1H, NH); m.p. 248° C. (decomp.); MS(EI) m/e 335 [M$^+$], 148, 91.

Example 21

5,7-dichloro-3-(4-methoxy-3-nitro-phenyl)-3-methyl-1H-quinoline-2,4-dione

The objective compound was prepared by the same procedure for the example 13, using a 4,6-dichloro-2-[2-(4-methoxy-3-nitro-phenyl)-propionylamino]-benzoic acid methyl ester (0.20 g, 0.47 mmol) and LiHMDS (1.40 mmol, 1M THF solution). After normal workup, the objective compound (120 mg, 71%) was obtained as yellow solid by a flash column chromatography (dichloromethane:methanol=30:1): $^1$H NMR (200 MHz, DMSO-$d_6$) δ 1.60 (s, 3H, $CH_3$), 3.86 (s, 3H, $OCH_3$), 7.05 (d, J=2.0 Hz, 1H, ArH), 7.29-7.37 (m, 2H, ArH), 7.61 (d, J=2.0 Hz, 1H, ArH); m.p. 255-256° C.; MS(EI) m/e 394 [M$^+$], 207, 132, 119; HRMS m/e cacld. for $C_{17}H_{12}N_2O_5Cl_2$ 394.0123, found 394.0114.

Example 22

5,7-dichloro-3-(4-hydroxy-3-nitro-phenyl)-3-methyl-1H-quinoline-2,4-dione

The objective compound was prepared by the same procedure for the example 13, using a 5,7-dichloro-3-(4-methoxy-3-nitro-phenyl)-3-methyl-1H-quinoline-2,4-dione (0.12 g, 0.30 mmol) and $BBr_3$ (0.90 mL, 1.0 M dichloromethane solution). After normal workup, the objective compound (50 mg, 48%) was obtained as pale yellow solid by a flash column chromatography (dichloromethane:methanol=30:1): $^1$H NMR (200 MHz, DMSO-$d_6$) δ 1.58 (s, 3H, $CH_3$), 7.05-7.09 (m, 2H, ArH), 7.14-7.31 (m, 2H, ArH), 7.61 (d, J=2.4 Hz, 1H, ArH); m.p. 239-240° C.; MS(EI) m/e 380 [M$^+$], 193, 165, 135; HRMS m/e cacld. for $C_{16}H_{10}N_2O_5Cl_2$ 379.9967, found 379.9968.

Example 23

3-(4-benzyloxy-3-bromo-phenyl)-5,7-dichloro-3-methyl-1H-quinoline-2,4-dione

The objective compound was prepared by the same procedure for the example 1, using a 2-[2-(4-benzyloxy-3-bromo-phenyl)-propionylamino]-4,6-dichloro-benzoic acid methyl ester (0.80 g, 1.50 mmol) and LiHMDS (3.20 mmol, 1M THF solution). After normal workup, the objective compound (0.51 g, 67%) was obtained as white solid by a flash column chromatography (n-hexane:EtOAc=5:1): $^1$H NMR (200 MHz, CDCl$_3$) δ 1.71 (s, 3H, CH$_3$), 5.09 (s, 2H, CH$_2$Ph), 6.78 (d, J=2.0 Hz, 1H, ArH), 6.85 (d, J=9.0 Hz, 1H, ArH), 7.04 (dd, J=8.6, 2.4 Hz, 1H, ArH), 7.11 (d, J=2.4 Hz, 1H, ArH), 7.33-7.43 (m, 5H, ArH); m.p. 189-190° C.; MS(EI) m/e 503 [M$^+$], 91; HRMS m/e cacld. for C$_{23}$H$_{16}$NO$_3$Br$_1$Cl$_2$ 502.9691, found 502.9696.

Example 24

3-(3-bromo-4-hydroxy-phenyl)-5,7-dichloro-3-methyl-1H-quinoline-2,4-dione

The objective compound was prepared by the same procedure for the example 13, using a 3-(4-benzyloxy-3-bromo-phenyl)-5,7-dichloro-3-methyl-1H-quinoline-2,4-dione (0.10 g, 0.20 mmol) and BBr$_3$ (0.59 mL, 1.0 M dichloromethane solution). After normal workup, the pure objective compound (65 mg, 78%) was obtained as white solid by a flash column chromatography (n-hexane:EtOAc=2:1): $^1$H NMR (200 MHz, CDCl$_3$) δ 1.70 (s, 3H, CH$_3$), 5.51 (br s, 1H, OH), 6.76 (d, J=1.6 Hz, 1H, ArH), 6.94 (d, J=8.6 Hz, 1H, ArH), 7.02 (d, J=2 Hz, 1H, ArH), 7.28 (dd, J=8.6, 2.4 Hz, 1H, ArH); m.p. 228-229° C.; MS(EI) m/e 413 [M$^+$], 381, 336, 299, 226; HRMS m/e cacld. for C$_{16}$H$_{10}$NO$_3$Br$_1$Cl$_2$ 412.9221, found 412.9195.

Example 25

3-[4-(1(S)-phenyl-ethyl-carbamoyl)-phenyl]-5,7-dichloro-3-methyl-1H-quinoline-2,4-dione A solution of 5,7-dichloro-3-(4-hydroxy-phenyl)-3-methyl-1H-quinoline-2,4-dione (0.45 g, 1.30 mmol) and triethylamine (0.18 mL) in dichloromethane (15 mL) was added (S)-methyl benzylisocyanate (0.15 g, 1.56 mmol) at 0° C. The reaction mixture was stirred for 20 hours at room temperature, and then poured into ice water (100 mL). The reaction mixture was extracted with dichloromethane (100 mL×3), washed with brine (100 mL×2), dried over anhydrous MgSO$_4$ and concentrated in vacuo. The residue was purified by a flash column chromatography (n-hexane:EtOAc=7:1) to afford the unseparable diastereomeric 1:1 mixture (0.50 g, 80%) of the objective diastereomers: $^1$H NMR (500 MHz, DMSO-d$_6$) δ 1.37 (d, J=7.0 Hz, 3H, CH$_3$), 1.54 (s, 3H, CH$_3$, one diastereomeric peaks), 1.64 (s, 3H, CH$_3$, the other diastereomeric peaks), 4.65 (q, 1H, CH), 7.01-7.3 (m, 11H, ArH), 8.35 (br s, 1H, NH), 11.28 (br s, 1H, NH); m.p. 110-115° C. (diastereomeric 1:1 mixture); MS(EI) m/e 483 [M$^+$−1], 335, 269, 120.

Example 26

3-[3-(1(S)-phenyl-ethyl-carbamoyl)-phenyl]-5,7-dichloro-3-methyl-1H-quinoline-2,4-dione The objective compound was prepared by the same procedure for the example 25, using a 5,7-dichloro-3-(3-hydroxy-phenyl)-3-methyl-1H-quinoline-2,4-dione (0.13 g, 0.40 mmol) and (S)-methylbenzylisocyanate (70.6 mg, 0.48 mmol) in the presence of triethylamine (0.40 mL). After normal workup, the unseparable diastereomeric 1:1 mixture of the objective diastereomers (0.15 g, 82%) was obtained as yellow solid by a flash column chromatography (n-hexane:EtOAc=8:1): $^1$H NMR (500 MHz, DMSO-d$_6$) δ 1.38 (d, J=7.1 Hz, 3H, CH$_3$), 1.54 (s, 3H, CH$_3$, one diastereomeric peaks), 1.64 (s, 3H, CH$_3$, the other diastereomeric peaks), 4.67 (q, 1H, CH), 6.79-7.34 (m, 11H, ArH), 8.35 (br s, 1H, NH), 11.28 (s, 1H, NH); m.p. 91-94° C.; MS(EI) m/e 483 [M$^+$−1], 336, 269, 120.

Example 27

3-(2,4-dibromo-phenyl)-5,7-dichloro-3-methyl-1H-quinoline-2,4-dione

To a solution of 3-(4-amino-phenyl)-5,7-dichloro-3-methyl-1H-quinoline-2,4-dione (84 mg, 0.25 mmol) in dry acetonitrile (10 mL) was added t-BuONO (50 μl, 0.38 mmol) at 0° C. After stirring for 15 minutes, CuBr$_2$ (141 mg, 0.63 mmol) was added thereto, and the reaction mixture was stirred additionally for 1 hour at 0° C. The resultant was poured into ice water (100 mL), and extracted with ethyl acetate (100 mL×3). The organic layer was washed with water (100 mL) and brine (100 mL×2), dried over anhydrous MgSO$_4$ after and concentrated in vacuo. The objective compound (73 mg, 73%) was obtained as white solid by a flash column chromatography (n-hexane:EtOAc=5:1): $^1$H NMR (200 MHz, CDCl$_3$) δ 1.74 (s, 3H, CH$_3$), 6.79-7.58 (m, 6H, ArH), 8.86 (s, 1H, NH).

Example 28

6,8-dibromo-3-(4-methoxy-3-nitro-phenyl)-3-methyl-1H-quinoline-2,4-dione

The objective compound was prepared by the same procedure for the example 1, using a 3,5-dibromo-2-[2-(4-methoxy-3-nitro-phenyl)-propionylamino]-benzoic acid methyl ester (0.65 g, 1.26 mmol) and LiHMDS (3.78 mmol, 1M solution in THF). After normal workup, the objective compound (160 mg, 27%) was obtained as white solid by a flash column chromatography (n-hexane:EtOAc=2:1): $^1$H NMR (200 MHz, DMSO-d$_6$) δ 1.68 (s, 3H, CH$_3$), 3.87 (s, 3H, OCH$_3$), 7.32 (d, J=9.0 Hz, 1H, ArH), 7.43 (dd, J=8.8, 2.4 Hz, 1H, ArH), 7.69 (d, J=2.4 Hz, 1H, ArH), 7.84 (d, J=2.6 Hz, 1H, ArH), 8.12 (d, J=2.6 Hz, 1H, ArH); MS(EI) m/e 482 [M$^+$], 277, 207, 102 ; HRMS m/e cacld. for C$_{17}$H$_{12}$N$_2$O$_5$Br$_2$ 481.9113, found 481.9122.

Example 29

3-(3-amino-4-methoxy-phenyl)-6,8-dibromo-3-methyl-1H-quinoline-2,4-dione

A solution of 6,8-dibromo-3-(4-methoxy-3-nitro-phenyl)-3-methyl-1H-quinoline-2,4-dione (0.14 g, 0.29 mmol) in acetic acid (5.0 mL) was treated with SnCl$_2$-2H$_2$O (0.26 g, 1.16 mmol) for 4 hours at room temperature. After the reaction was completed, yellow residue was obtained by evaporating solvent under reduced pressure. The residue was diluted with 1N HCl solution (200 mL), and was extracted with ethyl acetate (200 mL×3). The combined organic layer was washed with brine (200 mL×2) and water (200 mL×2) and dried over anhydrous MgSO$_4$. After evaporation of the solvent, the pure objective compound (56 mg, 42%) was obtained as yellow solid by a flash column chromatography (n-hexane:EtOAc=2:1): $^1$H NMR (200 MHz, CDCl$_3$) δ 1.73 (s, 3H, CH$_3$), 3.77 (s, 3H, OCH$_3$), 4.11 (br s, 2H, NH$_2$), 6.44-6.58 (m, 2H, ArH), 6.65 (d, J=8.6 Hz, 1H, ArH), 7.77 (d, J=2.2 Hz, 1H, ArH) ; HRMS m/e cacld. for $C_{17}H_{14}N_2O_3Br_2$ 451.9371, found 451.9385.

Example 30

3-(3-amino-4-hydroxy-phenyl)-6,8-dibromo-3-methyl-1H-quinoline-2,4-dione

The objective compound was prepared by the same procedure for the example 13, using a 3-(3-amino-4-methoxy-phenyl)-6,8-dibromo-3-methyl-1H-quinoline-2,4-dione (36 mg, 0.079 mmol) and $BBr_3$(0.4 mL, 1.0 M solution in dichloromethane). After normal workup, the pure objective compound (18 mg, 52%) was obtained as pale yellow solid by a flash column chromatography (n-hexane:EtOAc=3:1): $^1$H NMR (200 MHz, CDCl$_3$) δ 1.64 (s, 3H, CH$_3$), 4.85 (br s, 3H, NH$_2$ & OH), 6.41 (d, J=2.4 Hz, 1H, ArH), 6.37 (dd, J=8.6, 2.4 Hz, 1H, ArH), 6.55-6.61 (m, 2H, ArH), 7.86 (d, J=2.0 Hz, 1H, ArH); HRMS m/e cacld. for $C_{16}H_{12}N_2O_3Br_2$ 437.9215, found 437.9211.

Example 31

3-(4-hydroxy-3-methoxy-phenyl)-3-methyl-1H-quinoline-2,4-dione

The objective compound was prepared by the same procedure for the example 1, using a 2-[2-(4-hydroxy-3-methoxyphenyl)-propionyl amino]-benzoic acid methyl ester (1.00 g, 3.04 mmol) and LiHMDS (9.12 mmol, 1M solution in THF). After normal workup, the objective compound (0.46 g, 51%) was obtained as yellow solid by a flash column chromatography (n-hexane:EtOAc=5:1): $^1$H NMR (200 MHz, CDCl$_3$) δ 1.81 (s, 3H, CH$_3$), 3.83 (s, 3H, OCH$_3$), 5.55 (br s, 1H, OH), 6.76-6.87 (m, 4H, ArH), 7.12 (t, J=7.73 Hz, 1H, ArH), 7.49 (t, J=7.32 Hz, 1H, ArH), 7.90 (d, J=8.12 Hz, 1H, ArH), 8.17 (br s, 1H, NH); m.p. 168-169° C.; MS(EI) m/e 297 [M$^+$], 178, 150; HRMS m/e cacld. for $C_{17}H_{15}N_1O_4$ 297.1002, found 297.0999.

Example 32

3-(3,4-dihydroxy-phenyl)-3-methyl-1H-quinoline-2,4-dione

The objective compound was prepared by the same procedure for the example 13, using a 3-(4-hydroxy-3-methoxyphenyl)-3-methyl-1H-quinoline-2,4-dione (120 mg, 0.40 mmol) and BBr$_3$ (1.60 mL, 1.0 M solution in dichloromethane). After normal workup, the pure objective compound (71 mg, 62%) was obtained as pale yellow solid by a flash column chromatography (n-hexane:EtOAc=3:1): $^1$H NMR (200 MHz, DMSO-d$_6$) δ 1.57 (s, 3H, CH$_3$), 6.42 (dd, J=8.14, 2.03 Hz, 1H, ArH), 6.59-6.63 (m, 2H, ArH), 7.07 (t, J=7.73 Hz, 2H, ArH), 7.55 (t, J=7.32 Hz, 1H, ArH), 7.68 (d, J=7.32 Hz, 1H, ArH), 9.00 (br s, 1H, OH), 10.93 (br s, 1H, NH); m.p. 259-261° C.; MS(EI) m/e 283 [M$^+$], 268, 255, 237; HRMS m/e cacld. for $C_{16}H_{13}N_1O_4$ 283.0845, found 283.0849.

Example 33

3-(4-methoxy-phenyl)-3-methyl-1H-quinoline-2,4-dione

The objective compound was prepared by the same procedure for the example 1, using a 2-[2-(4-methoxy-phenyl)-propionyl amino]-benzoic acid methyl ester (1.00 g, 3.19 mmol) and LiHMDS (9.57 mmol, 1M solution in THF). After normal workup, the objective compound (0.51 g, 57%) was obtained as yellow solid by a flash column chromatography (n-hexane:EtOAc=5:1): $^1$H NMR (200 MHz, CDCl$_3$) δ 1.83 (s, 3H, CH$_3$), 3.73 (s, 3H, OCH$_3$), 6.77 d, J=8.9 Hz, 2H, ArH), 6.89-7.07 (m, 2H, ArH), 7.21 (d, J=8.9 Hz, 2H, ArH), 7.44-7.89 (m, 2H, ArH), 9.08 (br s, 1H).

Example 34

3-(4-hydroxy-phenyl)-3-methyl-1H-quinoline-2,4-dione

The objective compound was prepared by the same procedure for the example 13, using a 3-(4-methoxy-phenyl)-3-methyl-1H-quinoline-2,4-dione (1.00 g, 3.55 mmol) and BBr$_3$ (17.8 mL, 1.0 M solution in dichloromethane). After normal workup, the pure objective compound (0.47 g, 50%) was obtained as pale yellow solid by a flash column chromatography (n-hexane:EtOAc=5:1): $^1$H NMR (200 MHz, CDCl$_3$) δ 1.81 (s, 3H, CH$_3$), 5.20 (br s, 1H, OH), 6.68 (d, J=8.9 Hz, 2H, ArH), 6.85-7.19 (m, 4H, ArH), 7.45-7.89 (m, 2H, ArH), 8.46 (br s, 1H, NH).

Example 35

5-chloro-7-methoxy-3-(4-methoxy-phenyl)-3-methyl-1H-quinoline-2,4-dione

To a solution of 4,6-dichloro-2-[2-(4-methoxy-phenyl)-propionylamino]-benzoic acid methyl ester (1.00 g, 2.62 mmol) in dry THF (30 mL) was added NaH (0.32 g, 7.86 mmol, 60% dispersed in mineral oil) at room temperature. The reaction mixture was stirred for 10 hours at reflux temperature, and then poured into 1N HCl aqueous solution. The resulting mixture was extracted with ethyl acetate (100 mL×2). The organic layer was washed with brine (100 mL) and water (100 mL×2), dried over anhydrous MgSO$_4$, and concentrated in vacuo. The objective compound (0.36 g, 41%) was obtained as pale yellow solid by a flash column chromatography (n-hexane:EtOAc=2:1): $^1$H NMR (200 MHz, CDCl$_3$) δ 1.71 (s, 3H, CH$_3$), 3.71 (s, 3H, OCH$_3$), 3.89 (s, 3H, OCH$_3$), 6.46 (d, J=1.6 Hz, 1H, ArH) 6.56 (d, J=1.6 Hz, 1H, ArH), 6.77 (dd, J=6.9 Hz, 2.0 Hz, 2H, ArH), 7.14 (dd, J=6.9 Hz, 2.0 Hz, 2H, ArH), 8.77 (br s, 1H, NH); m.p. 222-224° C.; MS(EI) m/e 345 [M$^+$], 162, 134, 119, 91; HRMS m/e cacld. for $C_{18}H_{16}NO_4Cl$ 345.0768, found 345.0759.

Example 36

6,7-dichloro-3-methyl-3-(4-nitro-phenyl)-1H-quinoline-2,4-dione

To a suspension of 7-chloro-3-methyl-3-(4-nitro-phenyl)-1H-quinoline-2,4-diones (331 mg, 1.00 mmol) in glaicial acetic acid (15 ml) was added dropwise a solution of SO$_2$Cl$_2$ (300 µl, 3.00 mmol) at room temperature. The reaction mixture was stirred for 3 days at 60° C. After the reaction was qeunched by the addition of aqueous 1N NaOH solution (100 mL), the resulting mixture was extracted with ethyl acetate (100 mL×3). The organic layer was washed with brine (100 mL), dried over anhydrous MgSO$_4$, and concentrated in vacuo. The residue was purified by a flash column chromatography (n-hexane:EtOAc=6:1) to give objective compound (184 mg, 50%) as white solid: $^1$H NMR (200 MHz, DMSO-d$_6$) δ 1.75 (s, 3H, CH$_3$), 7.32 (d, J=1.2 Hz, 1H, ArH), 7.48-7.54 (dd, J=8.6, 2.0 Hz, 2H, ArH), 7.87 (d, J=1.2 Hz, 1H, ArH), 8.15-8.23 (dd, J=8.6, 2.0 Hz, 2H, ArH), 11.35 (br s, 1H, NH).

Example 37

7-chloro-3-methyl-3-(4-nitro-phenyl)-1H-quinoline-2,4-dione

To a suspension of a sodium hydride (1.5 g, 37.5 mmol, 60% in mineral oil) in dry DMF (50 mL) was added a solution of 4-chloro-2-[2-(4-nitro-phenyl)-propionyl amino]-benzoic acid methyl ester (6.4 g, 17.5 mmol) in dry DMF (20 mL) at 0° C. The reaction mixture was stirred for 30 minutes, and the reaction was qeunched by the addition of 0.5M HCl solution (100 mL). The resulting mixture was extracted with ethyl acetate (200 mL×3). The organic layer was washed with water (200 ml×2) and brine (200 ml×2), and dried over anhydrous $MgSO_4$. After evaporation fo the solvent, the residue was purified by a flash column chromatography (n-hexane:EtOAc=5:1) to provide the objective compound (5.50 g, 95%) as pale yellow solid: $^1$H NMR (200 MHz, $CDCl_3$) δ 1.93 (s, 3H, $CH_3$), 7.00 (d, J=1.8 Hz, 1H, ArH), 7.14 (dd, J=8.4, 2.0 Hz, 1H, ArH), 7.49 (d, J=9.2 Hz, 2H, ArH), 8.18 (d, J=9.2 Hz, 2H, ArH), 11.25 (br, 1H, NH); m.p. 209-210° C.; MS(EI) m/e 330 [M$^+$].

Example 38

3-(4-amino-phenyl)-7-chloro-3-methyl-1H-quinoline-2,4-dione

To a solution of 7-chloro-3-methyl-3-(4-nitro-phenyl)-1H-quinoline-2,4-dione (0.98 g, 2.96 mmol) in methanol (10 mL) was added $SnCl_2 \cdot 2H_2O$ (2.0 g, 8.88 mmol). The resulting solution was stirred at reflux temperature overnight. After the reaction was completed, the solvent was evaporated under reduced pressure to produce pale yellow residue. The residue was diluted with 1N HCl solution (200 mL) and extracted with ethyl acetate (200 mL×3). The organic layer was washed with brine (200 ml×2) and water (200 ml×2) and dried over anhydrous $MgSO_4$. After evaporation of the solvent, the objective compound (0.78 g, 88%) was obtained as pale yellow solid by purifying the residue with recrystallization (n-hexane:EtOAc=1:1): $^1$H NMR (200 MHz, $CDCl_3$) δ 1.79 (s, 3H, $CH_3$), 3.67 (br s, 2H, $NH_2$), 6.57 (d, J=8.6 Hz, 2H, ArH), 6.92 (d, J=2.0 Hz, 1H, ArH), 7.03-7.09 (m, 3H, ArH), 7.83 (d, J=8.8 Hz, 1H, ArH), 9.01 (br s, 1H, NH); m.p. 155-156° C.; MS(EI) m/e 300 [M$^+$].

Example 39

5,7-dichloro-3-methyl-3-(4-methylamino-phenyl)-1H-quinoline-2,4-dione

Example 40

5,7-dichloro-3-(4-dimethylamino-phenyl)-3-methyl-1H-quinoline-2,4-dione

A mixture of 3-(4-amino-phenyl)-5,7-dichloro-3-methyl-1H-quinoline-2,4-dione (235 mg, 0.70 mmol) and paraform aldehyde (63 mg, 2.10 mmol) in anhydrous methanol (25 mL) was treated with sodium borocyanohydride (44 mg, 0.70 mmol) at pH 6, adjusted with an acetic acid. The reaction was proceeded at room temperature until all the starting materials was disappeared. After evaporation of the solvent, the residue was diluted with 1N HCl solution (100 mL). The resulting suspension was extracted with ethyl acetate (100 mL×3). The combined organic layer was washed with water (100 ml) and brine (100 ml×2), dried over anhydrous $MgSO_4$, and concentrated in vacuo. The residue was purified by a flash column chromatography (n-hexane:EtOAc=8:1) to give two separable objective compounds of 5,7-dichloro-3-methyl-3-(4-methylamino-phenyl)-1H-quinoline-2,4-dione (21 mg, 6%, yellow solid) and 5,7-dichloro-3-(4-dimethylamino-phenyl)-3-methyl-1H-quinoline-2,4-dione (82 mg, 34%, pale yellow solid):

Example 39, $^1$H NMR (200 MHz, $CDCl_3$) (1.70 (s, 3H, $CH_3$), 2.78 (s, 3H, $HNCH_3$), 3.90 (s, 1H, $HNCH_3$), 6.48-6.52 (m, 2H, ArH), 6.78 (d, J=1.8 Hz, 1H, ArH), 6.98-7.02 (m, 2H, ArH), 7.07 (d, J=1.8 Hz, 1H, ArH), 8.85 (br s, 1H, NH); m.p. 268-269° C.; MS(EI) m/e 364 [M$^+$], 291, 250; HRMS m/e cacld. for $C_{18}H_{16}N_2O_2Cl_2$ 362.0589, found 362.0577;

Example 40, $^1$H NMR (200 MHz, $CDCl_3$) δ 1.70 (s, 3H, $CH_3$), 2.90 (s, 3H, $NCH_3$), 2.91 (s, 3H, $NCH_3$), 6.59-7.08 (m, 6H, ArH), 8.55 (s, 1H, NH); m.p. 185-186° C. MS(EI) m/e 348 [M$^+$], 333, 305, 291; HRMS m/e cacld. for $C_{17}H_{14}N_2O_2Cl_2$ 348.0432, found 348.0437.

Example 41

5,7-dichloro-3-methyl-3-(4-ethylamino-phenyl)-1H-quinoline-2,4-dione

Example 42

5,7-dichloro-3-(4-diethylamino-phenyl)-3-methyl-1H-quinoline-2,4-dione

The objective compound was prepared by the same procedure for the example 39 and 40, using a 3-(4-amino-phenyl)-5,7-dichloro-3-methyl-1H-quinoline-2,4-dione (235 mg, 0.70 mmol), acetaldehyde (148 mL, 2.10 mmol), and sodium borocyanohydride (44 mg, 0.70 mmol). After normal workup, The residue was purified by a flash column chromatography (n-hexane:EtOAc=8:1) to give two separable objective chemical compounds of 5,7-dichloro-3-methyl-3-(4-ethylamino-phenyl)-1H-quinoline-2,4-dione (10 mg, 4%, yellow solid) and 5,7-dichloro-3-(4-diethylamino-phenyl)-3-methyl-1H-quinoline-2,4-dione (220 mg, 87%, pale yellow solid):

Example 41, $^1$H NMR (200 MHz, $CDCl_3$) δ 1.20 (t, J=7.1 Hz, 3H, $CH_3$), 1.68 (s, 3H, $CH_3$), 3.08 (q, J=7.1 Hz, 2H, $NCH_2$), 3.63 (br s, 1H, NH), 6.45-6.52 (m, 2H, ArH), 6.74 (d, J=2.0 Hz, 1H, ArH), 6.94-7.00 (m, 2H, ArH), 7.06 (d, J=2.0 Hz, 1H, ArH), 8.48 (s, 1H, NH); m.p. 247-249° C.; MS(EI) m/e 390 [M$^+$], 375, 347; HRMS m/e cacld. for $C_{20}H_{20}N_2O_2Cl_2$ 390.0902, found 390.0912;

Example 42, $^1$H NMR (200 MHz, $CDCl_3$) δ 1.10 (t, J=7.1 Hz, 6H, 2×$CH_3$), 1.59 (s, 3H, $CH_3$), 3.28 (q, J=7.1 Hz, 4H, $NCH_2$), 6.51-6.56 (m, 2H, ArH), 6.79 (d, J=1.8 Hz, 1H, ArH), 6.98-7.02 (m, 2H, ArH), 7.07 (d, J=1.8 Hz, 1H, ArH), 9.05 (s, 1H, NH); m.p. 197-198° C.; MS(EI) m/e 362 [M$^+$], 364 [M$^+$+2]; HRMS m/e cacld. for $C_{18}H_{16}N_2O_2Cl_2$ 362.0588, found 362.0589.

Example 43

1-(R)-[3-(5,7-dichloro-3-methyl-2,4-dioxo-1,2,3,4-tetrahydro-quinoline-3-yl)-phenyl]-3-(1-(S)-phenyl-ethyl)-urea

Example 44

1-(S)-[3-(5,7-dichloro-3-methyl-2,4-dioxo-1,2,3,4-tetrahydro-quinoline-3-yl)-phenyl]-3-(1-(S)-phenyl-ethyl)-urea To a solution of 5,7-dichloro-3-(3-amino-phenyl)-3-methyl-1H-quinoline-2,4-dione (0.37 g, 1.40 mmol) and triethylamine (0.24 mL) in THF (20 mL) was added (S)-methylbenzylisocyanate (0.21 g, 1.40 mmol). The reaction mixture was extracted with ethyl acetate (100 mL×3), washed with brine (100 ml×2), dried over anhydrous MgSO$_4$, and concentrated in vacuo after. The residue was purified by a flash column chromatography (CH$_2$Cl$_2$:MeOH=30:1) to afford the diastereomeric 1:1 mixture (0.40 g, 71%) of the objective diastereomers as yellow solid. The analytical samples of each diastereomer were obtained by separation on preliminary TLC:

Example 43, $^1$H NMR (500 MHz, DMSO-d$_6$) δ 1.04 (s, 3H, CH$_3$), 1.32 (d, J=6.9 Hz, 3H, CH$_3$), 4.72 (q, 1H, CH), 5.31 (s, 1H, NH), 6.33 (s, 1H, NH), 6.85 (m, 2H, ArH), 6.98 (m, 1H, ArH), 7.13-7.18 (m, 4H, ArH), 10.16 (s, 1H, NH); m.p. 115-120° C.;

Example 44, $^1$H NMR (500 MHz, DMSO-d$_6$) δ 1.00 (s, 3H, CH$_3$), 1.32 (d, J=6.9 Hz, 3H, CH$_3$), 4.71 (q, 1H, CH), 5.29 (d, J=4.2 Hz, 1H, NH), 6.34 (d, J=4.5 Hz, 1H, NH), 6.81 (m, 2H, ArH), 6.96 (m, 1H, ArH), 7.14-7.36 (m, 4H, ArH), 10.15 (s, 1H, NH); m.p. 126-132° C.

Example 45

7-chloro-3-(2,4-dibromo-phenyl)-3-methyl-1H-quinoline-2,4-dione

The objective compound was prepared by the same procedure for the example 27, using a 3-(4-amino-phenyl)-7-chloro-3-methyl-1H-quinoline-2,4-dione (151 mg, 0.50 mmol), t-BuONO (100 μl, 0.75 mmol), and CuBr$_2$ (280 mg, 1.25 mmol). After normal workup, the pure objective compound (149 mg, 82%) was obtained as white solid by a flash column chromatography (n-hexane:EtOAc=5:1): $^1$H NMR (200 MHz, CDCl$_3$) δ 1.83 (s, 3H, CH$_3$), 6.90-7.89 (m, 7H, ArH), 8.42 (br s, 1H, NH).

Example 46

5-chloro-3-(4-methoxy-phenyl)-3-methyl-7-(4-methyl-piperazine-1-yl)-1H-quinoline-2,4-dione A mixture of 5,7-dichloro-3-(4-methoxy-phenyl)-3-methyl-1H-quinoline-2,4-dione (0.10 g, 0.29 mmol) and 1-methylpiperazine (3.0 mL) was heated at reflux temperature overnight. Excessive 1-methylpiperazine was removed by evaporation in vacuo. The residue was diluted with water (50 mL), and resulting suspension was extracted with ethyl acetate (50 mL×3). The organic layer was washed with brine (50 ml×2), dried over anhydrous MgSO$_4$, and concentrated under reduced pressure. The pure objective compound (38 mg, 32%) was obtained as yellow solid by a flash column chromatography (CH$_2$Cl$_2$:MeOH=20:1): $^1$H NMR (200 MHz, CDCl$_3$) δ 1.82 (s, 3H, CH$_3$), 2.33 (s, 3H, NCH$_3$), 2.44-2.65 (m, 4H, 2×NCH$_2$), 2.88-2.91 (m, 4H, 2×NCH$_2$), 3.74 (s, 3H, OCH$_3$), 6.43 (d, J=1.8 Hz, 1H, ArH) 6.54 (d, J=1.8 Hz, 1H, ArH), 6.80 (d, J=9.0 Hz, 1H, ArH), 7.19 (d, J=9.0 Hz, 1H, ArH), 9.23 (s, 1H, NH); m.p. 201-202° C.; MS(EI) m/e 413 [M$^+$]; HRMS m/e cacld. for C$_{22}$H$_{24}$N$_3$O$_3$Cl$_1$ 413.1506, found 413.1516.

Example 47

5-chloro-3-(4-hydroxy-phenyl)-3-methyl-7-(4-methyl-piperazine-1-yl)-1H-quinoline-2,4-dione The objective compound was prepared by the same procedure for the example 13, using a 5-chloro-3-(4-methoxy-phenyl)-3-methyl-7-(4-methyl-piperazine-1-yl)-1H-quinoline-2,4-dione (0.03 g, 0.07 mmol) and BBr$_3$(0.22 mL, 1.0 M dichloromethane solution). After normal workup, the pure objective compound (19 mg, 65%) was obtained as slightly yellow solid by recrytalization (n-hexane:EtOAc=1:3): $^1$H NMR (200 MHz, CDCl$_3$) δ 1.75 (s, 3H, CH$_3$), 2.38 (s, 3H, NCH$_3$), 2.59-2.65 (m, 4H, 2×NCH$_2$), 2.89-2.92 (m, 4H, 2×NCH$_2$), 3.33 (s, 3H, OCH$_3$), 6.52-6.55 (m, 2H, ArH), 6.69-6.74 (m, 2H, ArH), 7.04-7.08 (m, 2H, ArH).

Example 48

3-(4-amino-phenyl)-5-chloro-3-methyl-7-(4-methyl-piperazine-1-yl)-1H-quinoline-2,4-dione A mixture of 3-(4-amino-phenyl)-5,7-dichloro-3-methyl-1H-quinoline-2,4-dione (0.1 g, 0.30 mmol) and 1-methylpiperazine (36 mL, 0.36 mmol) in dry pyridine (5.0 mL) was heated at reflux temperature overnight. After evaporation of the solvent in vacuo, the residue was diluted with water (50 mL), and resulting suspension was extracted with ethyl acetate (50 mL×3). The organic layer was washed with brine (50 mL×2) and dried over anhydrous MgSO$_4$ concentrated under reduced pressure. The pure objective compound (87 mg, 73%) was obtained as yellow solid by a flash column chromatography (CH$_2$Cl$_2$:MeOH=20:1): $^1$H NMR (200 MHz, CDCl$_3$) δ 1.78 (s, 3H, CH$_3$) 2.35 (s, 3H, NCH$_3$), 2.43-2.67 (m, 4H, NCH$_2$), 2.90-2.95 (m, 4H, NCH$_2$), 3.67 (br s, 2H, NH$_2$), 6.38 (d, J=1.8 Hz, 1H, ArH), 6.54-6.61 (m, 3H, ArH), 7.04 (d, J=8.6 Hz, 2H, ArH), 8.44 (br s, 1H, NH).

Example 49

5-chloro-3-methyl-7-(4-methyl-piperazine-1-yl)-3-(4-nitro-phenyl)-1H-quinoline-2,4-dione A mixture of 3-(4-nitro-phenyl)-5,7-dichloro-3-methyl-1H-quinoline-2,4-dione (0.3 g, 0.82 mmol) and 1-methylpiperazine (123 mL, 1.23 mmol) in dry pyridine (5.0 mL) was heated at reflux temperature for 5 hours. After evaporation of the solvent in vacuo, the residue was diluted with water (100 mL), and the resulting suspension was extracted with ethyl acetate (100 mL×3). The organic layer was washed with brine (100 mL×2), dried over anhydrous MgSO$_4$ concentrated under reduced pressure. The pure objective compound (0.16 g, 46%) was obtained as yellow solid by a flash column chromatography (CH$_2$Cl$_2$:MeOH=20:1): $^1$H NMR (200 MHz, CDCl$_3$) δ 1.90 (s, 3H, CH$_3$), 2.34 (s, 3H, NCH$_3$), 2.54-2.59 (m, 4H, NCH$_2$), 2.88-3.07 (m, 4H, NCH$_2$), 6.43 (d, J=1.8 Hz, 1H, ArH), 6.64 (d, J=2.0 Hz, 1H, ArH), 7.46 (d, J=9.0 Hz, 2H, ArH), 8.17 (d, J=9.0 Hz, 2H, ArH), 8.64 (br s, 1H, NH).

Example 50

3-(4-amino-phenyl)-3-methyl-7-(4-methyl-piperazine-1-yl)-1H-quinoline-2,4-dione

A mixture of 3-(4-amino-phenyl)-5,7-chloro-3-methyl-1H-quinoline-2,4-dione (0.15 g, 0.5 mmol) and 1-methylpiperazine (3.0 mL) was heated at reflux temperature overnight. Excessive 1-methylpiperazine was removed by evaporation in vacuo. The residue was diluted with water (50 mL), and the resulting suspension was extracted with ethyl acetate (50 mL×3). The organic layer was washed with brine (50 ml×2), dried over anhydrous MgSO$_4$, and concentrated under reduced pressure. The pure objective compound (86 mg, 47%) was obtained as yellow solid by a flash column chromatography (CH$_2$Cl$_2$:MeOH=20:1): $^1$H NMR (200 MHz, CDCl$_3$) δ 1.78 (s, 3H, ArH), 2.34 (s, 3H, NCH$_3$), 2.49-2.54 (m, 4H, NCH$_2$), 3.34-3.39 (m, 4H, NCH$_2$), 3.60 (br s, 2H, NH$_2$), 6.10 (d, J=2.2 Hz, 1H, ArH), 6.52-6.60 (m, 3H, ArH), 7.10 (d, J=8.8 Hz, 2H, ArH), 7.80 (d, J=9.0 Hz, 1H, ArH), 8.21 (br, 1H, NH); m.p. 265-267° C.; MS(EI) m/e 364 [M$^+$].

Example 51

3-methyl-7-(4-methyl-piperazine-1-yl)-3-(4-nitro-phenyl)-1H-quinoline-2,4-dione

A mixture of 3-(4-nitro-phenyl)-7-chloro-3-methyl-1H-quinoline-2,4-dione (0.3 g, 0.90 mmol) and 1-methylpiperazine (3.0 mL) was heated at reflux temperature overnight. Excessive 1-methylpiperazine was removed by evaporation in vacuo. The residue was diluted with water (50 mL), and the resulting suspension was extracted with ethyl acetate (50 mL×3). The organic layer was washed with brine (50 ml×2), dried over anhydrous MgSO$_4$, and concentrated under reduced pressure. The pure objective compound (0.11 g, 31%) was obtained as yellow solid by a flash column chromatography (CH$_2$Cl$_2$: MeOH=20:1): $^1$H NMR (200 MHz, CDCl$_3$) δ 1.90 (s, 3H, CH$_3$), 2.35 (s, 3H, NCH$_3$), 2.50-2.55 (m, 4H, NCH$_2$), 3.35-3.44 (m, 4H, NCH$_2$), 6.13 (d, J=2.4 Hz, 1H, ArH), 6.64 (dd, J=9.2, 2.4 Hz, 1H, ArH), 7.52 (d, J=9.0 Hz, 2H, ArH), 7.82 (d, J=8.8 Hz, 1H, ArH), 8.15 (d, J=9.2 Hz, 2H, ArH); m.p. 150-151° C.; MS(EI) m/e 394 [M$^+$].

Example 52

3-(4-bromo-phenyl)-5-chloro-7-methoxy-3-methyl-1H-quinoline-2,4-dione

To a solution of 3-(4-bromo-phenyl)-5,7-dichloro-3-methyl-1H-quinoline-2,4-dione (600 mg, 1.40 mmol) in dry THF (30 mL) was added NaH (140 mg, 3.50 mmol) at 0° C. and stirred for 1 hour at room temperature. The reactant was poured into a 0.5N HCl solution and extracted with ethyl acetate (100 mL×3). The organic layer was washed with brine (100 mL×2), dried over anhydrous MgSO$_4$, and concentrated in vacuo. The pure objective compound (260 mg, 47%) was obtained as white solid by a flash column chromatography (n-hexane:EtOAc=5:1): $^1$H NMR (200 MHz, CDCl$_3$) δ 1.73 (s, 3H, CH$_3$), 3.91 (s, 3H, OCH$_3$), 6.48 (d, J=1.6 Hz, 1H, ArH), 6.60 (d, J=1.6 Hz, 1H, ArH), 7.11-7.44 (m, 4H, ArH), 8.62 (br s, 1H, NH); m.p. 239-240° C.; MS(EI) m/e 393 [M$^+$], 210, 183; HRMS m/e cacld. for C$_{17}$H$_{13}$N$_1$O$_3$Br$_1$Cl$_1$ 392.9767, found 392.9760.

Structures of chemical compounds prepared by the above examples are listed in Table 1.

TABLE 1

| Example | Structural Formula |
|---|---|
| 1 | 5,7-dichloro-3-methyl-3-phenyl-1H-quinoline-2,4-dione |
| 2 | 3-methyl-3-phenyl-1H-quinoline-2,4-dione |
| 3 | 7-chloro-3-methyl-3-phenyl-1H-quinoline-2,4-dione |
| 4 | 5,7-dibromo-3-methyl-3-phenyl-1H-quinoline-2,4-dione |
| 5 | 5-chloro-7-methoxy-3-methyl-3-phenyl-1H-quinoline-2,4-dione |
| 6 | 5-methoxy-7-chloro-3-methyl-3-phenyl-1H-quinoline-2,4-dione |
| 7 | 5-bromo-7-methoxy-3-methyl-3-phenyl-1H-quinoline-2,4-dione |
| 8 | 5,7-dimethoxy-3-methyl-3-phenyl-1H-quinoline-2,4-dione |
| 9 | 6,7-dichloro-3-methyl-3-phenyl-1H-quinoline-2,4-dione |

TABLE 1-continued
| Example | Structural Formula |
|---|---|
| 10 | |
| 11 | |
| 12 | |
| 13 | |
| 14 | |
| 15 | |
| 16 | |
| 17 | |
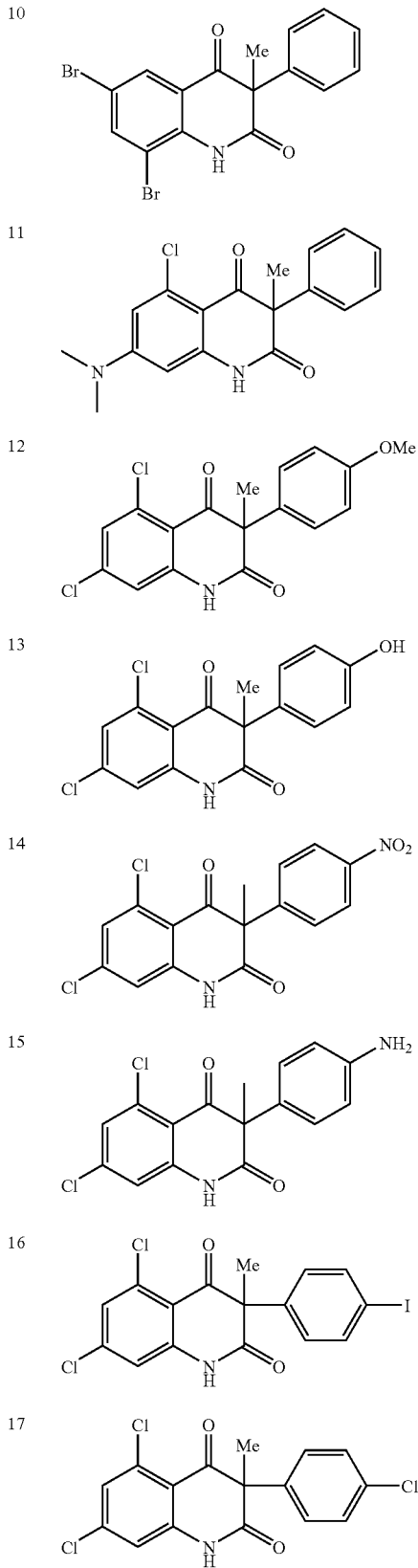
TABLE 1-continued
| Example | Structural Formula |
|---|---|
| 18 | |
| 19 | |
| 20 | |
| 21 | |
| 22 | |
| 23 | |
| 24 | |
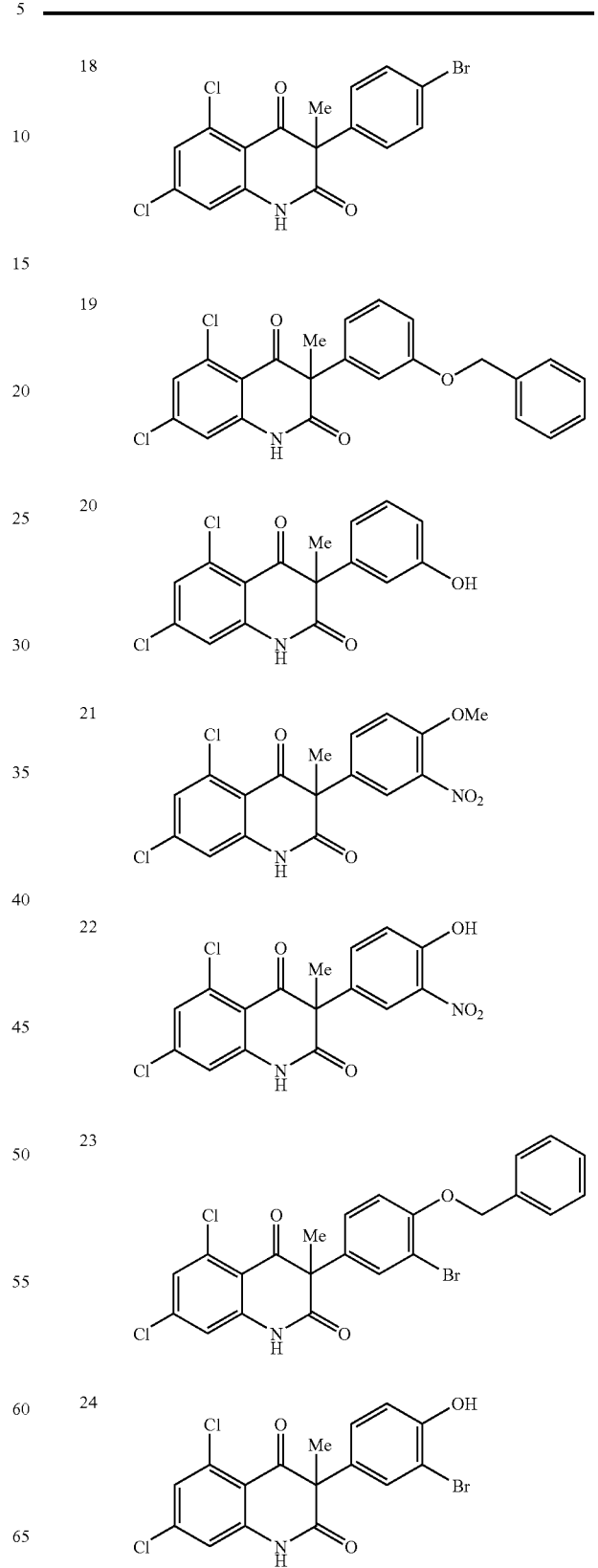

TABLE 1-continued
| Example | Structural Formula |
|---------|-------------------|
| 25 | 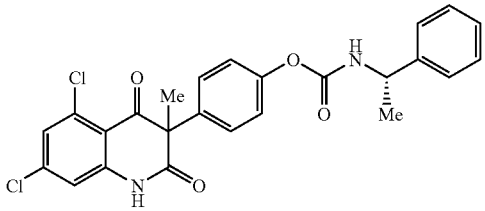 |
| 26 | 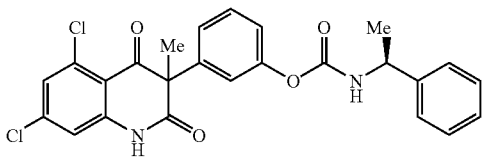 |
| 27 | 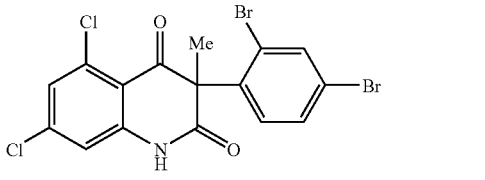 |
| 28 | 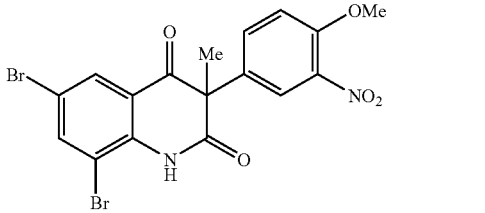 |
| 29 | 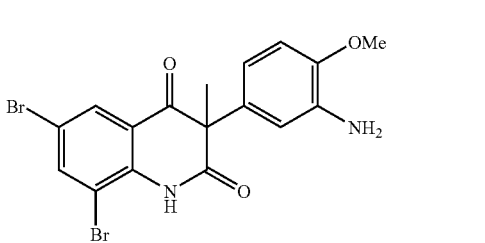 |
| 30 | 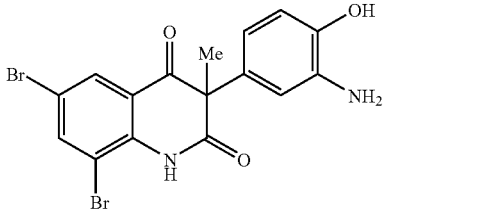 |
| 31 | 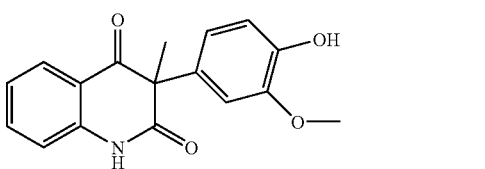 |
| 32 | 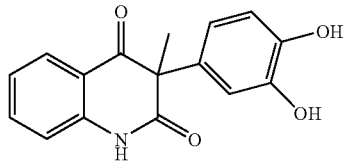 |
| 33 | 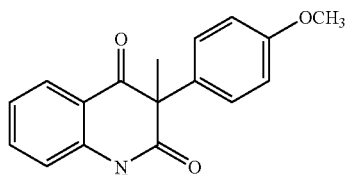 |
| 34 | 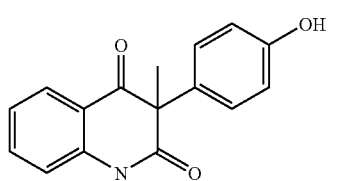 |
| 35 | 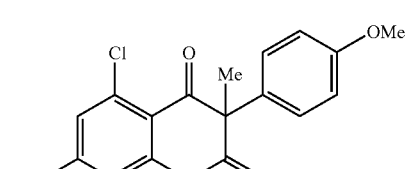 |
| 36 | 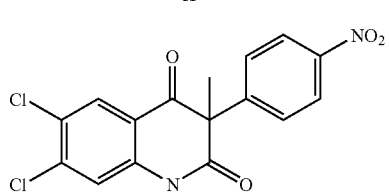 |
| 37 | 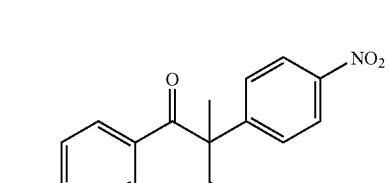 |
| 38 | 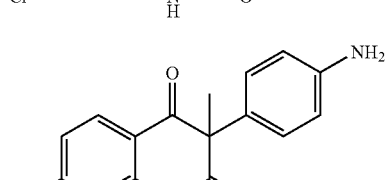 |
| 39 | 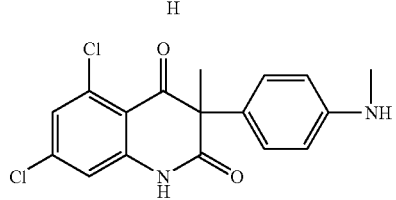 |

TABLE 1-continued

| Example | Structural Formula |
|---|---|
| 40 | 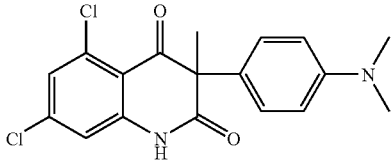 |
| 41 | 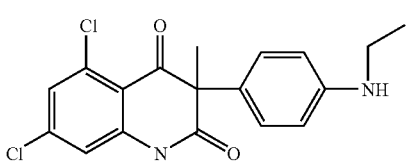 |
| 42 | 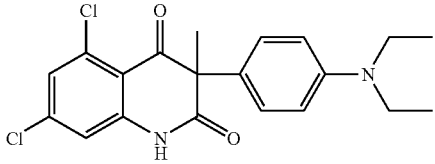 |
| 43 | 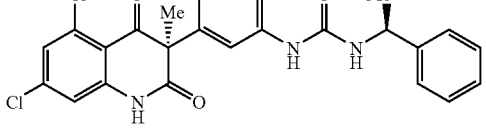 |
| 44 | 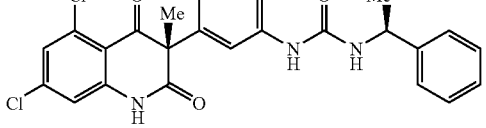 |
| 45 | 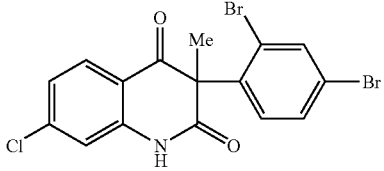 |
| 46 | 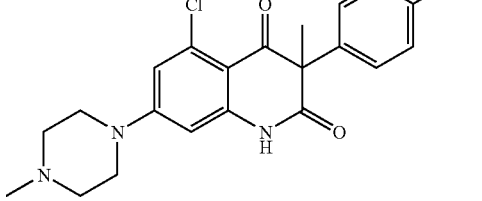 |
| 47 | 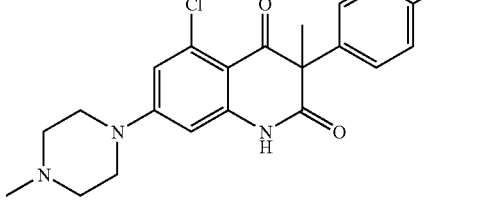 |
| 48 | 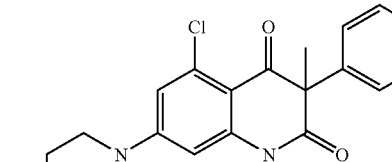 |
| 49 | 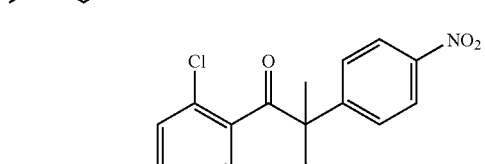 |
| 50 | 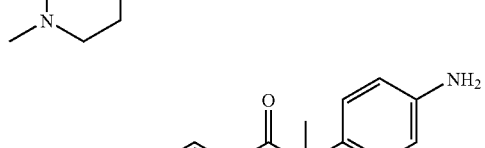 |
| 51 | 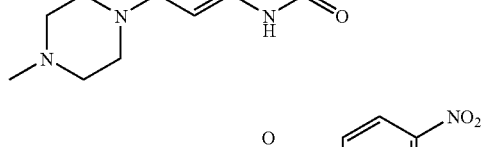 |
| 52 | 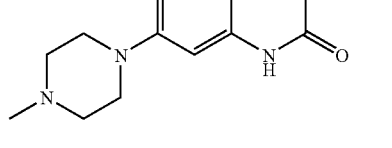 |

Experimental Example 1

Expression of Human Serotonin 5-HT6 Receptor

Human serotonin 5-HT6 receptor protein was expressed in insect cell as described below. Human 5-HT6 cDNA was cloned from human brain cDNA library (Clontech, Palo Alto, USA) by PCR amplification using 5'-TCATCTGCTTTC-CCGCCACCCTAT-3' for forward and 5'-TCAGGGTCTGGGTTCTGCTCAATC-3' for reverse. Amplified cDNA fragments were introduced into pGEMT easy vector (Promega, Madison, USA) and then DNA sequencing was performed to confirm receptor DNA sequence. Serotonin 5-HT6 clone was subcloned into insect cell expression vector BacPAK8 (Clontech). pBacPAK8/5-HT6 was transfected into insect Sf21 cell (Clontech) and protein expression of 5-HT6 receptor was confirmed by SDS PAGE and receptor binding assay. Cell lysis was performed by sonication for 2 minutes at 4° C. and cell debris was discarded by centrifugation for 10 min at 3,000×g. Membrane fraction was purified partially from supernatant above by centrifugation for 1 hr at 100,000×g.

Experimental Example 2

Binding at Cloned 5-HT6 Receptors

[$^3$H]LSD (lysergic acid diethylamide) binding assay was performed in 96-well plate to test the binding affinities of the compounds according to the present invention on 5-HT6 receptor. The cloned receptor membranes (9 μg/well) were used in a final volume of 0.25 ml reaction mixture and incubated at 37° C. for 60 min with 50 mM Tris-HCl buffer (pH 7.4) involving 10 mM $MgCl_2$ and 0.5 mM EDTA. For drug screening, testing compounds were incubated as described above, in a reaction mixture containing 1.87 nM of [$^3$H]LSD. After incubation, the reaction was terminated by the rapid filtration and washed with ice-cold 50 mM Tris-HCl buffer using a Inotech harvester (Inotech, Switzerland) through Wallac GF/C glass fiber filter (Wallac, Finland) which was pre-soaked in 0.5% PEI. The filter was covered with MeltiLex, sealed in a sample bag followed by drying in the oven, and counted by MicroBeta Plus (Wallac, Finland). Competition binding studies were carried out with 7-8 concentrations of the test compound run in duplicate tubes, and isotherms from three assays were calculated by computerized nonlinear regression analysis (GraphPad Prism Program, San Diego, Canada) to yield median inhibitory concentration ($IC_{50}$) values. Non-specific binding was determined in the presence of 10 μM methiothepin. All testing compounds were dissolved in dimethylsulfoxide (DMSO), and serially diluted to various concentrations for binding assays. 5-HT6 receptor binding affinities of the target examples were shown in Table 2.

TABLE 2

| ID | $IC_{50}$(μM) |
|---|---|
| Example 1 | 0.089 |
| Example 2 | 1.078 |
| Example 3 | 2.471 |
| Example 4 | 0.320 |
| Example 5 | 0.560 |
| Example 6 | 0.428 |
| Example 7 | 0.119 |
| Example 8 | 0.118 |
| Example 9 | 1.058 |
| Example 10 | 1.330 |
| Example 11 | 1.162 |
| Example 12 | 0.917 |
| Example 13 | 0.020 |
| Example 14 | 0.870 |
| Example 15 | 0.254 |

TABLE 2-continued

| ID | $IC_{50}$(μM) |
|---|---|
| Example 16 | 1.548 |
| Example 17 | 1.426 |
| Example 18 | 0.494 |
| Example 19 | 0.134 |
| Example 20 | 0.049 |
| Example 21 | 1.226 |
| Example 22 | 1.009 |
| Example 23 | 1.256 |
| Example 24 | 0.126 |
| Example 25 | 0.816 |
| Example 26 | 0.980 |
| Example 27 | 0.349 |
| Example 28 | 1.203 |
| Example 29 | 1.549 |
| Example 30 | 1.725 |
| Example 31 | 0.801 |
| Example 32 | 0.769 |
| Example 33 | 0.487 |
| Example 34 | 1.260 |
| Example 35 | 1.364 |
| Example 36 | 0.645 |
| Example 37 | 1.003 |
| Example 38 | 0.585 |
| Example 39 | 0.418 |
| Example 40 | 0.563 |
| Example 41 | 0.046 |
| Example 42 | 0.015 |
| Example 43 | 1.115 |
| Example 44 | 0.791 |
| Example 45 | 2.219 |
| Example 46 | 1.46 |
| Example 47 | 1.063 |
| Example 48 | 1.078 |
| Example 49 | 1.023 |
| Example 50 | 0.942 |
| Example 51 | 0.904 |
| Example 52 | 0.073 |

Examples 1, 12, 13, 20, 41, 42 and 52 showed almost same affinities as or better affinities than known selective antagonists known in the prior art.

Experimental Example 3

Radioligand Binding Studies for 5-HT6 Receptor Selectivity

The following tests were performed to survey how much the compound showing excellent affinity to 5-HT6 receptor in experiment 2 has selectivity with regard to 5-HT6 receptor, compared to other dopamine receptors and 5-HT receptors.

(1) Binding Assays of 5-HT Receptor Family

Radioligand bindings were performed according to the test method provided by the supplier of receptor membrane (Euroscreen/BioSignal Packard Inc.). Detailed assay condition were shown in the following Table 3.

TABLE 3

| | $5\text{-}HT_{1a}$ | $5\text{-}HT_{2a}$ | $5\text{-}HT_{2c}$ | $5\text{-}HT_7$ |
|---|---|---|---|---|
| Origin | Stable CHO-K1 cell strain expressing human recombinant receptors (Euroscreen/BioSignal) | | | |
| Binding buffer solution | 50 mM Tris-HCl (pH 7.4) 10 mM MgSO4 0.5 mM EDTA 0.1% ascorbic acid | 50 mM Tris-HCl (pH 7.4) | 50 mM Tris-HCl (pH 7.7) 0.1% ascorbic acid 10 μM Pargyline | 50 mM Tris-HCl (pH 7.4) 10 mM MgSO4 0.5 mM EDTA |

TABLE 3-continued

|  | 5-HT$_{1a}$ | 5-HT$_{2a}$ | 5-HT$_{2c}$ | 5-HT$_7$ |
|---|---|---|---|---|
| Final volume | 250 µl | 250 µl | 250 µl | 250 µl |
| Membrane content | 40 µg | 15 µg | 4 µg | 10 µg |
| Radioligand | [$^3$H]8-OH-DPAT 0.5 nM | [$^3$H]Ketanserin 1 nM | [$^3$H]Mesulergine 1 nM | [$^3$H] LSD 3 nM |
| Non-specific Binding | methiothepin 0.5 µM | Mianserin 1 µM | methiothepin 10 µM | methiothepin 10 µM |
| Incubation | 27° C., 60 min | 37° C., 15 min | 37° C., 30 min | 27° C., 120 min |
| Filtration | GF/C, 0.3% PEI | GF/C, 0.05% Brij | GF/C, 1% BSA | GF/C, 0.3% PEI |

(2) Binding Assays of Dopamine Receptor Family

The radioligands used were [$^3$H] spiperone (for hD$_{2L}$ and hD$_3$ receptors, 1 nM) and [$^3$H]YM-09151-2 (for hD4.2 receptor, 0.06 nM). Radioligand bindings were performed by the protocols provided by the supplier of receptor membranes (BioSignal Packard Inc., Montreal, Canada). Briefly, the buffer used in D$_2$ or D$_3$ receptor binding assay was 50 mM Tris-HCl (pH 7.4), 10 mM MgCl$_2$, 1 mM EDTA, or 50 mM Tris-HCl (pH 7.4), 5 mM MgCl$_2$, 5 mM EDTA, 5 mM KCl, 1.5 mM CaCl$_2$, 120 mM NaCl, respectively. In [$^3$H] YM-09151-2 receptor binding assays, the buffer containing 50 mM Tris-HCl (pH 7.4), 5 mM MgCl$_2$, 5 mM EDTA, 5 mM KCl and 1.5 mM CaCl$_2$ was used. Nonspecific binding was determined with haloperidol (10 µM) or clozapine (10 µM) for D$_2$ and D$_3$, and D$_4$ receptors, respectively. Competition binding studies were carried out with 7-8 concentrations of the test compound run in duplicate tubes, and isotherms from three assays were calculated by computerized nonlinear regression analysis (GraphPad Prism Program, San Diego, Canada) to yield median inhibitory concentration (IC$_{50}$) values. The dopamine and serotonin receptor subtypes selectivity of compounds according to the present invention is shown in Table 4.

TABLE 4

| ID | Binding affinity (Inhibition rate % at 10 µM) | | | | | | | | |
|---|---|---|---|---|---|---|---|---|---|
| ID | D1 | D2 | D3 | D4 | 5HT1a | 5HT2a | 5HT2c | 5HT6 | 5HT7 |
| Example 1 | 11.4 | 1.6 | 12.6 | 0.0 | 16.4 | 6.4 | 18.3 | 91.1 | 43.2 |
| Example 2 | 10.2 | 5.6 | 12.2 | 0.0 | 15.0 | 8.4 | 30.6 | 73.2 | 10.4 |
| Example 3 | 25.5 | 4.9 | 10.9 | 0.0 | 40.2 | 12.0 | 8.9 | 69.0 | 7.0 |
| Example 4 | 23.7 | 3.0 | 15.8 | 0.0 | 11.7 | 13.6 | 29.8 | 70.9 | 13.0 |
| Example 5 | 10.3 | 20.5 | 10.1 | 0.0 | 18.9 | 26.8 | 20.5 | 73.5 | 9.4 |
| Example 6 | 31.1 | 29.7 | 23.0 | 1.6 | 65.8 | 10.6 | 13.5 | 68.3 | 19.5 |
| Example 7 | 30.5 | 12.8 | 1.5 | 0.8 | 29.1 | 25.4 | 30.3 | 71.1 | 12.4 |
| Example 8 | 16.9 | 16.0 | 4.6 | 0.8 | 30.2 | 13.6 | 23.9 | 74.0 | 23.3 |
| Example 9 | 26.2 | 8.2 | 10.8 | 0.0 | 45.2 | 16.6 | 30.4 | 71.2 | 10.8 |
| Example 10 | 13.5 | 11.2 | 19.5 | 0.0 | 0.0 | 29.5 | 16.8 | 73.4 | 20.7 |
| Example 11 | 40.5 | 19.3 | 20.5 | 0.4 | 49.5 | 30.4 | 20.0 | 70.7 | 35.2 |
| Example 12 | 15.7 | 16.3 | 24.0 | 0.0 | 40.2 | 8.5 | 5.7 | 73.3 | 23.1 |
| Example 13 | 51.0 | 35.2 | 27.8 | 0.0 | 33.9 | 48.6 | 39.4 | 89.5 | 36.7 |
| Example 14 | 6.5 | 26.5 | 30.7 | 0.0 | 60.5 | 54.1 | 3.8 | 71.2 | 10.8 |
| Example 15 | 4.8 | 0.0 | 5.8 | 4.5 | 52.3 | 16.9 | 15.6 | 73.0 | 11.1 |
| Example 16 | 24.7 | 20.1 | 10.0 | 1.3 | 43.5 | 47.2 | 34.5 | 70.9 | 50.7 |
| Example 17 | 13.8 | 7.5 | 16.5 | 0.5 | 26.7 | 30.2 | 21.2 | 69.8 | 26.9 |
| Example 18 | 37.7 | 16.0 | 12.5 | 0.0 | 8.0 | 16.9 | 10.7 | 73.8 | 7.8 |
| Example 19 | 92.6 | 37.8 | 37.4 | 0.0 | 88.8 | 67.3 | 0.0 | 74.9 | 69.5 |
| Example 20 | 64.6 | 10.9 | 13.2 | 0.0 | 0.0 | 46.1 | 4.7 | 91.7 | 29.2 |
| Example 21 | 40.2 | 10.5 | 16.4 | 0.0 | 15.9 | 16.3 | 10.8 | 73.7 | 0.0 |
| Example 22 | 35.7 | 11.2 | 34.0 | 0.0 | 68.7 | 50.9 | 2.5 | 72.5 | 36.3 |
| Example 23 | 16.8 | 9.6 | 32.5 | 0.7 | 64.9 | 26.4 | 21.9 | 70.6 | 27.4 |
| Example 24 | 13.0 | 5.0 | 16.6 | 0.0 | 50.4 | 11.5 | 22.8 | 71.0 | 5.5 |
| Example 25 | 54.1 | 8.4 | 10.2 | 0.0 | 35.9 | 16.7 | 4.0 | 69.8 | 30.6 |
| Example 26 | 50.5 | 26.5 | 14.8 | 0.5 | 0.0 | 38.1 | 9.1 | 70.0 | 12.7 |
| Example 27 | 25.8 | 10.2 | 15.6 | 1.6 | 46.0 | 30.8 | 28.1 | 71.1 | 12.3 |
| Example 28 | 46.9 | 9.4 | 40.9 | 2.3 | 60.9 | 9.0 | 13.7 | 73.2 | 10.2 |
| Example 29 | 23.6 | 5.6 | 43.8 | 11.6 | 40.7 | 21.1 | 40.6 | 68.5 | 28.1 |
| Example 30 | 18.6 | 18.5 | 25.1 | 0.9 | 0.0 | 35.1 | 5.4 | 69.2 | 4.9 |
| Example 31 | 37.1 | 9.2 | 9.8 | 0.0 | 31.2 | 43.5 | 10.2 | 70.6 | 16.4 |
| Example 32 | 39.0 | 16.0 | 12.6 | 0.0 | 13.5 | 26.9 | 31.9 | 71.0 | 20.1 |
| Example 33 | 29.5 | 20.9 | 13.1 | 0.0 | 20.4 | 10.7 | 13.5 | 72.4 | 6.6 |
| Example 34 | 15.8 | 17.3 | 25.4 | 0.0 | 19.8 | 13.5 | 20.1 | 70.8 | 0.9 |
| Example 35 | 43.1 | 5.1 | 6.4 | 1.7 | 52.3 | 20.7 | 16.4 | 69.1 | 22.4 |
| Example 36 | 12.6 | 16.5 | 11.9 | 0.0 | 42.1 | 13.2 | 8.2 | 71.9 | 16.5 |
| Example 37 | 49.2 | 8.3 | 10.5 | 0.0 | 10.4 | 49.2 | 1.4 | 73.3 | 21.0 |
| Example 38 | 44.3 | 16.5 | 16.8 | 5.8 | 51.9 | 31.5 | 20.7 | 74.1 | 17.4 |
| Example 39 | 38.5 | 19.8 | 8.4 | 10.2 | 23.0 | 12.1 | 13.1 | 72.0 | 9.1 |
| Example 40 | 40.8 | 10.5 | 4.5 | 0.0 | 50.2 | 42.2 | 6.5 | 67.2 | 30.3 |
| Example 41 | 24.0 | 25.2 | 12.6 | 0.0 | 15.7 | 10.8 | 14.0 | 67.7 | 15.4 |

TABLE 4-continued

| ID | Binding affinity (Inhibition rate % at 10 μM) | | | | | | | | |
|---|---|---|---|---|---|---|---|---|---|
| ID | D1 | D2 | D3 | D4 | 5HT1a | 5HT2a | 5HT2c | 5HT6 | 5HT7 |
| Example 42 | 38.7 | 15.7 | 25.3 | 8.5 | 6.5 | 16.9 | 13.7 | 69.5 | 10.1 |
| Example 43 | 30.1 | 5.7 | 24.0 | 6.1 | 18.0 | 21.3 | 0.0 | 70.6 | 5.0 |
| Example 44 | 35.0 | 11.5 | 16.2 | 0.0 | 25.4 | 58.5 | 21.5 | 73.8 | 32.2 |
| Example 45 | 42.3 | 13.0 | 5.6 | 0.0 | 60.3 | 23.0 | 31.6 | 66.0 | 29.5 |
| Example 46 | 16.0 | 30.4 | 16.7 | 7.2 | 25.4 | 16.5 | 10.7 | 67.1 | 17.8 |
| Example 47 | 20.9 | 27.2 | 14.2 | 12.8 | 27.1 | 42.8 | 12.4 | 71.9 | 16.3 |
| Example 48 | 27.4 | 19.6 | 8.7 | 0.0 | 35.0 | 37.2 | 2.5 | 71.6 | 5.6 |
| Example 49 | 26.0 | 10.5 | 12.4 | 0.0 | 1.4 | 33.4 | 19.8 | 70.2 | 24.4 |
| Example 50 | 34.1 | 8.2 | 50.1 | 0.0 | 6.7 | 21.5 | 15.4 | 74.5 | 20.5 |
| Example 51 | 40.9 | 7.4 | 13.5 | 0.0 | 44.2 | 26.4 | 20.3 | 73.5 | 17.5 |
| Example 52 | 41.5 | 9.3 | 7.4 | 0.0 | 7.8 | 30.6 | 20.0 | 89.6 | 8.8 |
| SB-271046 | 49.7 | 17.3 | 66.2 | 14.2 | 84.2 | 60.1 | 64.3 | 100.0 | 34.9 |

As shown in table 4, the compounds according to the present invention show very excellent 5-HT6 receptor selectivity by 100~500 times and show also better selectivity, when compared with known selective antagonist SB-271046.

Experimental Example 4

In Vitro Functional Studies

By a method (2000) disclosed by Rutledge et al. of MDS Pharma Service (Bothell, Wash., USA, MDSPS PT# 1037161), activity of adenylil cyclase in HeLa cell having transfected with human 5-HT6 receptor was measured. The assay mixture consisted of Hanks' balanced salt solution (HBSS, pH 7.4) containing: 1 mM $MgCl_2$, 1 mM $CaCl_2$, 100 mM 1-methyl-3-isobutylxanthine. Incubation was started by addition of membrane suspension and compounds according to the present invention. Following the a 20 minutes incubation at 37° C., intracellular cAMP levels were measured by EIA (enzyme-immunoassay), and a compound showing inhibitory effects on serotonin (5-HT)-stimulated camp accumulation was classified into an antagonist.

Among the compounds according to the present invention, example 1 and 13 having excellent receptor affinity and a typical skeleton structure was identified as a 5-HT6 receptor antagonist and showed a weaker antagonist activity than methiothepin, a nonselective antagonist. However, it has higher potential as a medicine because of its excellent selectivity. Inhibitory effects of example 1, 13 and methiothepin on serotonin (5-HT)-stimulated cAMP accumulation using HeLa cell line were shown in FIG. 1.

Experimental Example 5

Inhibitory Effect on Methamphetamine-Induced Hyperactivity and Stereotypy in Rats On the day of testing, rats (200-250 g) were put into a transparent polycarbonate cages located in the activity chamber, and adapted for 30 minutes. For a methamphetamine-induced activity, vehicle or compounds according to the present invention was injected (i.p.) 30 minutes before the injection of methamphetamine (2 mg/kg, i.p.). After systemic injection of methamphetamine, total movement distance traveled or total stereotypy was measured over the 120-minutes period using an activity analyzer (TruScan, Coulbourn Instruments, USA).

Figure 2A:
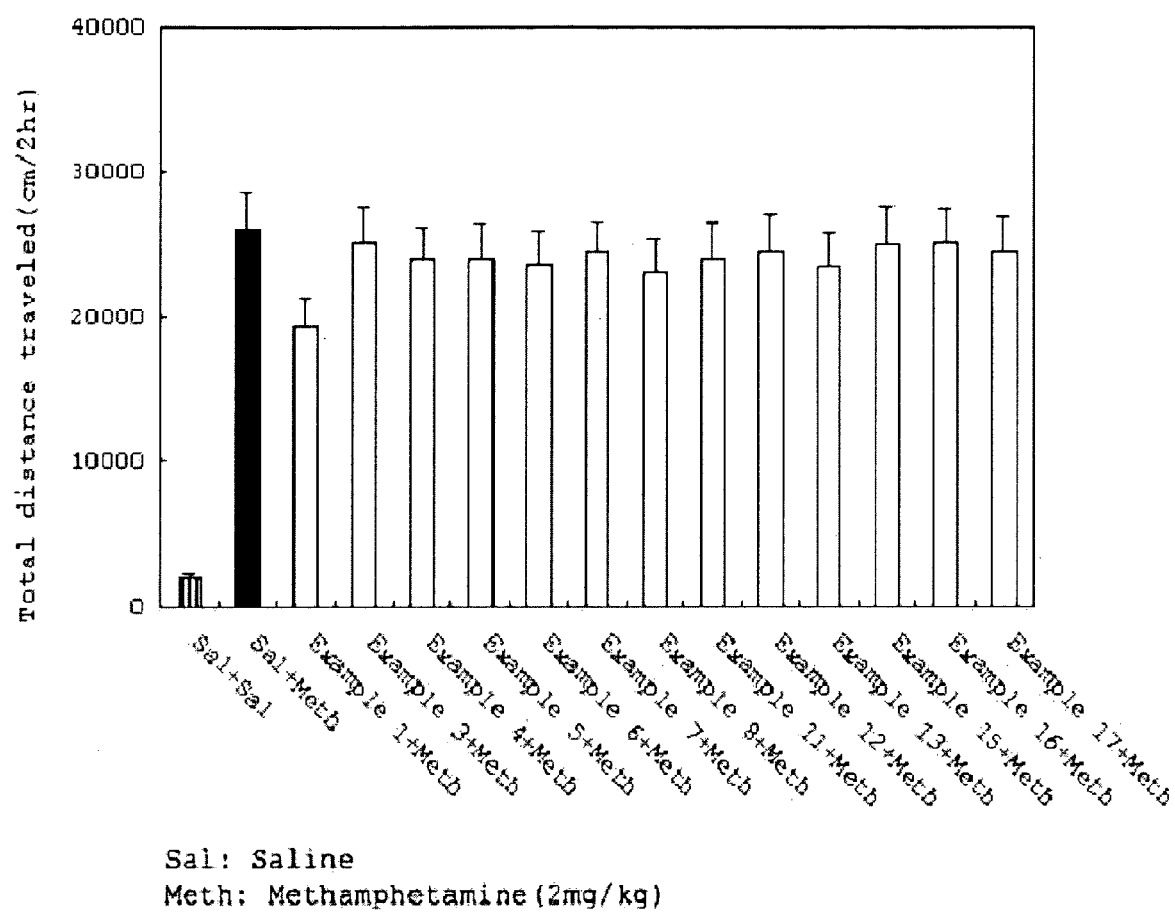
FIG. 2 is a graphs showing an inhibitory effect of compounds (50 mg/kg, i.p.) according to the present invention on hyperactivity of a rat induced by methamphetamine (2 mg/kg, i.p.).
Figure 2B:
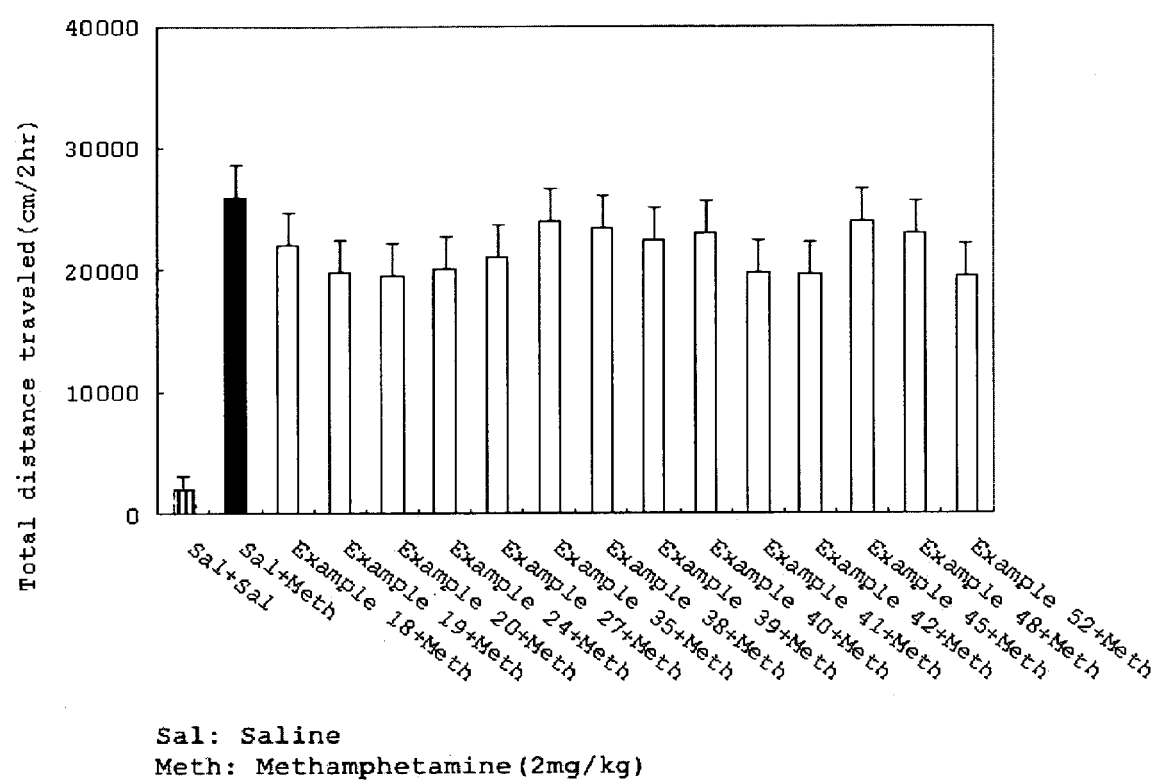
Figure 3A:
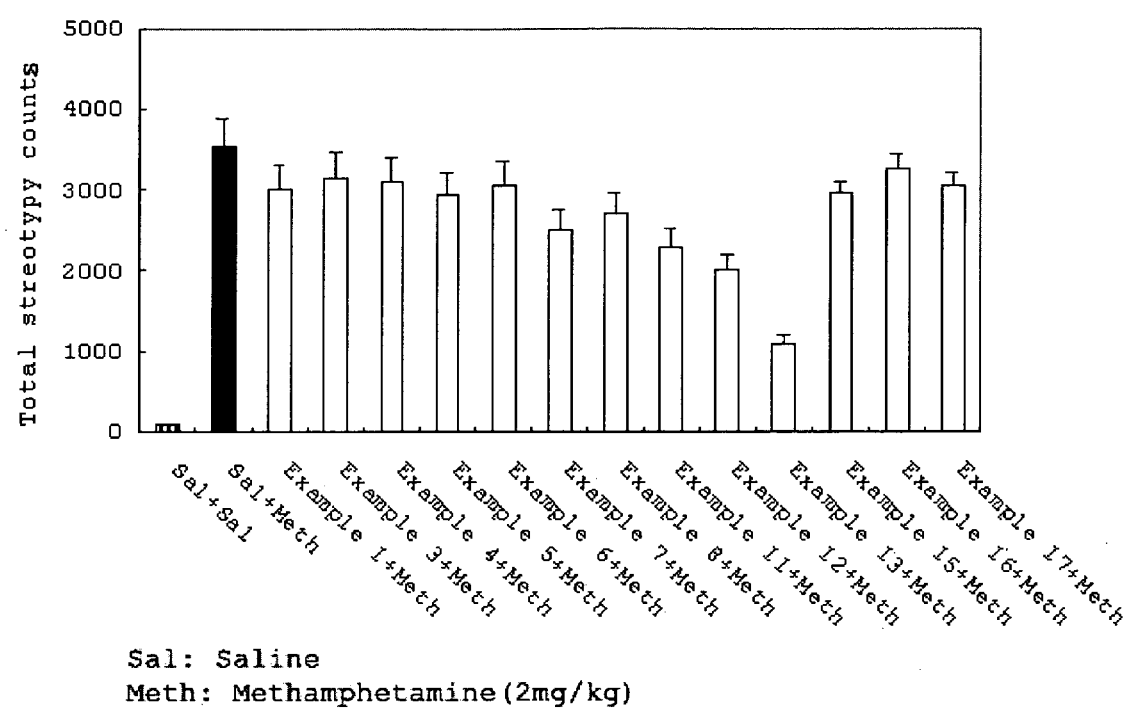
FIG. 3 is a graphs showing an inhibitory effect of compounds (50 mg/kg, i.p.) according to the present invention on stereotypic behaviors of a rat induced by methamphetamine (2 mg/kg, i.p.).
Figure 3B:
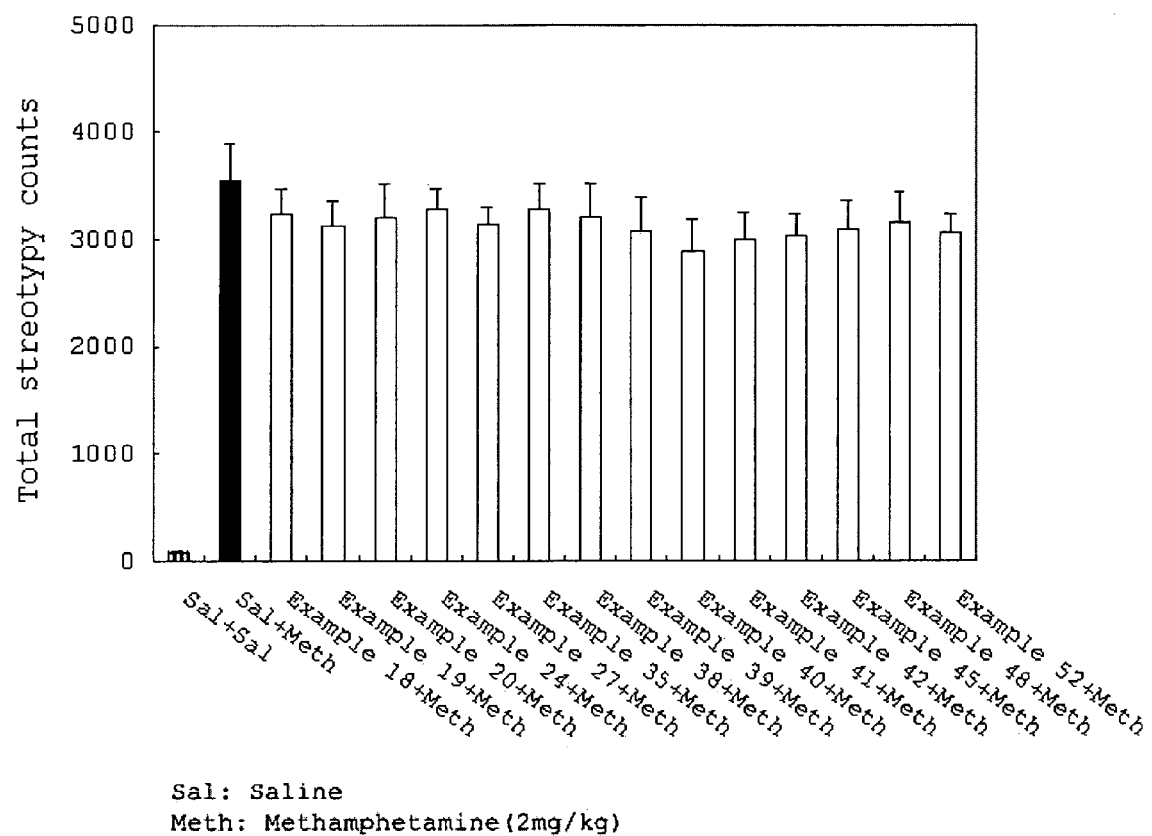

The inhibitory effect of compounds (50 mg/kg, i.p.) of the present invention on methamphetamine (2 mg/kg, i.p.)-induced hyperactivity in rats is shown in FIGS. 2(a) and 2(b). The inhibitory effects of compounds (50 mg/kg, i.p.) of the present invention on methamphetamine (2 mg/kg, i.p.)-induced stereotypy is shown in FIGS. 3(a) and 3(b).

It was found out that the compounds of examples 1 and 13 having excellent 5-HT6 receptor affinity and selectivity show a mild antipsychotic effect.

What is claimed is:

1. A compound of 3-aryl-3-methyl-quinoline-2,4-dione selected from the group consisting of:
- 5,7-dichloro-3-methyl-3-phenyl-1H-quinoline-2,4-dione;
- 7-chloro-3-methyl-3-phenyl-1H-quinoline-2,4-dione;
- 5,7-dibromo-3-methyl-3-phenyl-1H-quinoline-2,4-dione;
- 5-chloro-7-methoxy-3-methyl-3-phenyl-1H-quinoline-2,4-dione;
- 7-chloro-5-methoxy-3-methyl-3-phenyl-1H-quinoline-2,4-dione;
- 5-bromo-7-methoxy-3-methyl-3-phenyl-1H-quinoline-2,4-dione;
- 5,7-dimethoxy-3-methyl-3-phenyl-1H-quinoline-2,4-dione;
- 6,7-dichloro-3-methyl-3-phenyl-1H-quinoline-2,4-dione;
- 6,8-dibromo-3-methyl-3-phenyl-1H-quinoline-2,4-dione;
- 5-chloro-7-dimethylamino-3-methyl-3-phenyl-1H-quinoline-2,4-dione;
- 5,7-dichloro-3-(4-methoxy-phenyl)-3-methyl-1H-quinoline-2,4-dione;
- 5,7-dichloro-3-(4-hydroxy-phenyl)-3-methyl-1H-quinoline-2,4-dione;
- 5,7-dichloro-3-methyl-3-(4-nitro-phenyl)-1H-quinoline-2,4-dione;
- 3-(4-amino-phenyl)-5,7-dichloro-3-methyl-1H-quinoline-2,4-dione;
- 5,7-dichloro-3-(4-iodo-phenyl)-3-methyl-1H-quinoline-2,4-dione;
- 5,7-dichloro-3-(4-chloro-phenyl)-3-methyl-1H-quinoline-2,4-dione;
- 3-(4-bromo-phenyl)-5,7-dichloro-3-methyl-1H-quinoline-2,4-dione;
- 3-(3-benzyloxy-phenyl)-5,7-dichloro-3-methyl-1H-quinoline-2,4-dione;
- 3-(3-hydroxy-phenyl)-5,7-dichloro-3-methyl-1H-quinoline-2,4-dione;
- 5,7-dichloro-3-(4-methoxy-3-nitro-phenyl)-3-methyl-1H-quinoline-2,4-dione;
- 5,7-dichloro-3-(4-hydroxy-3-nitro-phenyl)-3-methyl-1H-quinoline-2,4-dione;
- 3-(4-benzyloxy-3-bromo-phenyl)-5,7-dichloro-3-methyl-1H-quinoline-2,4-dione;
- 3-(3-bromo-4-hydroxy-phenyl)-5,7-dichloro-3-methyl-1H-quinoline-2,4-dione;
- 3-[4-(1(S)-phenyl-ethyl-carbamoyl)-phenyl]-5,7-dichloro-3-methyl-1H-quinoline-2,4-dione;
- 3-[3-(1(S)-phenyl-ethyl-carbamoyl)-phenyl]-5,7-dichloro-3-methyl-1H-quinoline-2,4-dione;
- 3-(2,4-dibromo-phenyl)-5,7-dichloro-3-methyl-1H-quinoline-2,4-dione;
- 6,8-dibromo-3-(4-methoxy-3-nitro-phenyl)-3-methyl-1H-quinoline-2,4-dione;
- 3-(3-amino-4-methoxy-phenyl)-6,8-dibromo-3-methyl-1H-quinoline-2,4-dione;
- 3-(3-amino-4-hydroxy-phenyl)-6,8-dibromo-3-methyl-1H-quinoline-2,4-dione;
- 3-(4-hydroxy-3-methoxy-phenyl)-3-methyl-1H-quinoline-2,4-dione;
- 3-(3,4-dihydroxy-phenyl)-3-methyl-1H-quinoline-2,4-dione;
- 3-(4-methoxy-phenyl)-3-methyl-1H-quinoline-2,4-dione;
- 3-(4-hydroxy-phenyl)-3-methyl-1H-quinoline-2,4-dione;
- 5-chloro-7-methoxy-3-(4-methoxy-phenyl)-3-methyl-1H-quinoline-2,4-dione;
- 6,7-dichloro-3-methyl-3-(4-nitro-phenyl)-1H-quinoline-2,4-dione;
- 7-chloro-3-methyl-3-(4-nitro-phenyl)-1H-quinoline-2,4-dione;
- 3-(4-amino-phenyl)-7-chloro-3-methyl-1H-quinoline-2,4-dione;
- 5,7-dichloro-3-methyl-3-(4-methylamino-phenyl)-1H-quinoline-2,4-dione;
- 5,7-dichloro-3-(4-dimethylamino-phenyl)-3-methyl-1H-quinoline-2,4-dione;
- 5,7-dichloro-3-methyl-3-(4-ethylamino-phenyl)-1H-quinoline-2,4-dione;
- 5,7-dichloro-3-(4-diethylamino-phenyl)-3-methyl-1H-quinoline-2,4-dione;
- 1-(R)-[3-(5,7-dichloro-3-methyl-2,4-dioxo-1,2,3,4-tetrahydro-quinoline-3-yl)-phenyl]-3-(1-(S)-phenyl-ethyl)-urea;
- 1-(S)-[3-(5,7-dichloro-3-methyl-2,4-dioxo-1,2,3,4-tetrahydro-quinoline-3-yl)-phenyl]-3-(1-(S)-phenyl-ethyl)-urea;
- 7-chloro-3-(2,4-dibromo-phenyl)-3-methyl-1H-quinoline-2,4-dione;
- 5-chloro-3-(4-methoxy-phenyl)-3-methyl-7-(4-methyl-piperazine-1-yl)-1H-quinoline-2,4-dione;
- 5-chloro-3-(4-hydroxy-phenyl)-3-methyl-7-(4-methyl-piperazine-1-yl)-1H-quinoline-2,4-dione;
- 3-(4-amino-phenyl)-5-chloro-3-methyl-7-(4-methyl-piperazine-1-yl)-1H-quinoline-2,4-dione;
- 5-chloro-3-methyl-7-(4-methyl-piperazine-1-yl)-3-(4-nitro-phenyl)-1H-quinoline-2,4-dione;
- 3-(4-amino-phenyl)-3-methyl-7-(4-methyl-piperazine-1-yl)-1H-quinoline-2,4-dione;
- 3-methyl-7-(4-methyl-piperazine-1-yl)-3-(4-nitro-phenyl)-1H-quinoline-2,4-dione; and
- 3-(4-bromo-phenyl)-5-chloro-7-methoxy-3-methyl-1H-quinoline-2,4-dione.

2. A method for preparing the compound of claim 1, comprising the steps of:
 (i) coupling a derivative of 2-methyl-2-arylethanoic acid and a derivative of 2-aminobenzoic acid in the presence of a coupling agent to form an amide; and
 (ii) cyclizing the amide obtained in step (i) under basic condition to form the compound of claim 3.

3. The method according to claim 2, wherein the amide is prepared by:

reacting a derivative of 2-methyl-2-arylethanoic acid with a chlorinating agent in an inert solvent to form an acid chloride; and mixing and heating the acid chloride and a derivative of 2-aminobenzoic acid in an inert solvent.

4. A pharmaceutical composition comprising the compound of claim 1 or a pharmaceutically acceptable salt thereof as an active ingredient.

* * * * *

SEQUENCE LISTING

<160> NUMBER OF SEQ ID NOS: 2

<210> SEQ ID NO 1
<211> LENGTH: 24
<212> TYPE: DNA
<213> ORGANISM: Artificial Sequence
<220> FEATURE:
<223> OTHER INFORMATION: primer

<400> SEQUENCE: 1
tcatctgctt tcccgccacc ctat                                          24

<210> SEQ ID NO 2
<211> LENGTH: 24
<212> TYPE: DNA

```
<213> ORGANISM: Artificial Sequence
<220> FEATURE:
<223> OTHER INFORMATION: primer

<400> SEQUENCE: 2
tcagggtctg ggttctgctc aatc                                           24
```